(12) United States Patent
Nguyen et al.

(10) Patent No.: US 8,690,936 B2
(45) Date of Patent: Apr. 8, 2014

(54) EXPANDABLE SHEATH FOR INTRODUCING AN ENDOVASCULAR DELIVERY DEVICE INTO A BODY

(75) Inventors: Duy Nguyen, Corona, CA (US); Kim Nguyen, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 711 days.

(21) Appl. No.: 12/249,867

(22) Filed: Oct. 10, 2008

(65) Prior Publication Data

US 2010/0094392 A1 Apr. 15, 2010

(51) Int. Cl.
*A61F 2/06* (2013.01)

(52) U.S. Cl.
USPC .......................... 623/1.11; 606/191

(58) Field of Classification Search
USPC ............... 623/1.11, 1.23, 1.12, 1.26, 1.3; 606/191–199; 604/103.14, 272, 264, 604/103.06, 93.01, 523, 536; 600/184; 156/54

See application file for complete search history.

(56) References Cited

U.S. PATENT DOCUMENTS

| | | | |
|---|---|---|---|
| 4,601,713 A * | 7/1986 | Fuqua | 604/514 |
| 4,710,181 A * | 12/1987 | Fuqua | 604/514 |
| 4,716,901 A | 1/1988 | Jackson et al. | |
| 4,738,666 A | 4/1988 | Fuqua | |
| 4,921,479 A * | 5/1990 | Grayzel | 604/509 |
| 5,104,388 A * | 4/1992 | Quackenbush | 604/264 |
| 5,158,545 A | 10/1992 | Trudell et al. | |
| 5,176,659 A | 1/1993 | Mancini | |
| 5,217,468 A | 6/1993 | Clement | |
| 5,234,425 A | 8/1993 | Fogarty et al. | |
| 5,256,150 A | 10/1993 | Quiachon et al. | |
| 5,318,588 A | 6/1994 | Horzewski et al. | |
| 5,380,304 A | 1/1995 | Parker | |
| 5,514,091 A | 5/1996 | Yoon | |
| 5,514,236 A | 5/1996 | Avellanet et al. | |
| 5,810,776 A * | 9/1998 | Bacich et al. | 604/131 |
| 5,827,227 A | 10/1998 | DeLago | |
| 5,895,410 A | 4/1999 | Forber et al. | |
| 5,964,730 A | 10/1999 | Williams et al. | |
| 5,997,508 A | 12/1999 | Lunn et al. | |
| 6,090,072 A | 7/2000 | Kratoska et al. | |
| 6,090,136 A * | 7/2000 | McDonald et al. | 623/1.23 |

(Continued)

FOREIGN PATENT DOCUMENTS

EP 0177177 9/1986
EP 0249456 12/1987

(Continued)

*Primary Examiner* — Katherine Dowe
*Assistant Examiner* — Katrina Stansky
(74) *Attorney, Agent, or Firm* — David L. Hauser; Pui Tong Ho

(57) ABSTRACT

Embodiments of an expandable sheath can be used in conjunction with a catheter assembly to introduce a prosthetic device, such as a tissue heart valve, into a patient. Such embodiments can minimize trauma to the vessel by allowing for temporary expansion of a portion of the introducer sheath to accommodate the delivery apparatus, followed by a return to the original diameter once the prosthetic device passes through. Some embodiments can comprise a sheath with inner and outer tubular layers, and an intermediate tubular layer comprising a shape memory alloy. Other embodiments comprise one or more layers having one or more longitudinal notches or cuts to facilitate expansion of the sheath. Embodiments of the present expandable sheath can avoid the need for multiple insertions for the dilation of the vessel, thus offering advantages over prior art introducer sheaths.

18 Claims, 20 Drawing Sheets

(56) References Cited

U.S. PATENT DOCUMENTS

| | | |
|---|---|---|
| 6,494,860 B2 | 12/2002 | Rocamora et al. |
| 6,632,236 B2 * | 10/2003 | Hogendijk .................... 606/198 |
| 6,814,715 B2 * | 11/2004 | Bonutti et al. ........... 604/164.03 |
| 6,899,727 B2 * | 5/2005 | Armstrong et al. .......... 623/1.12 |
| 7,144,386 B2 | 12/2006 | Korkor et al. |
| 7,329,268 B2 | 2/2008 | Van Nguyen et al. |
| 7,534,250 B2 | 5/2009 | Schaeffer et al. |
| 7,785,360 B2 * | 8/2010 | Freitag ........................ 623/1.11 |
| 2002/0032459 A1 * | 3/2002 | Horzewski et al. ........... 606/198 |
| 2004/0087968 A1 | 5/2004 | Core |
| 2005/0085842 A1 * | 4/2005 | Eversull et al. ............... 606/191 |
| 2005/0124937 A1 | 6/2005 | Kick et al. |
| 2005/0222576 A1 | 10/2005 | Kick et al. |
| 2006/0020321 A1 * | 1/2006 | Parker .......................... 623/1.12 |
| 2006/0135981 A1 | 6/2006 | Lenker et al. |
| 2006/0217755 A1 * | 9/2006 | Eversull et al. ............... 606/191 |
| 2007/0021768 A1 | 1/2007 | Nance et al. |
| 2007/0074805 A1 * | 4/2007 | Leeflang et al. ................ 156/84 |
| 2008/0200943 A1 | 8/2008 | Barker et al. |
| 2008/0243081 A1 | 10/2008 | Nance et al. |

FOREIGN PATENT DOCUMENTS

| | | |
|---|---|---|
| EP | 0385920 | 5/1990 |
| WO | WO9219312 | 11/1992 |
| WO | WO9307812 | 4/1993 |
| WO | WO03002181 | 1/2003 |
| WO | WO2004002562 | 1/2004 |
| WO | WO2005018728 | 3/2005 |
| WO | WO2007035471 | 3/2007 |
| WO | WO2008002915 | 1/2008 |
| WO | WO2008042311 | 4/2008 |

* cited by examiner

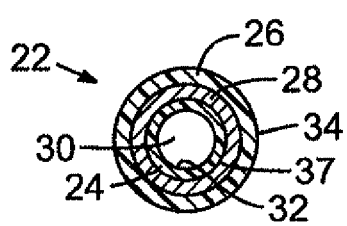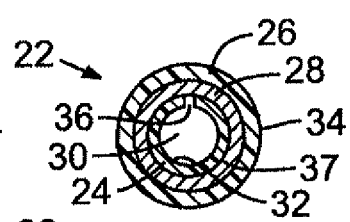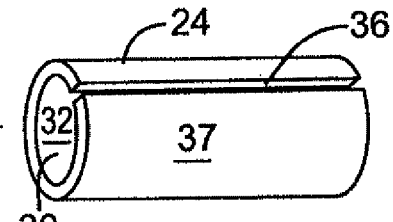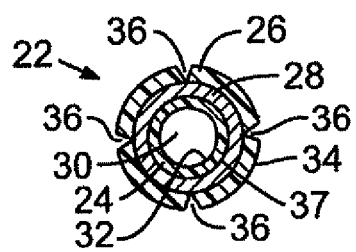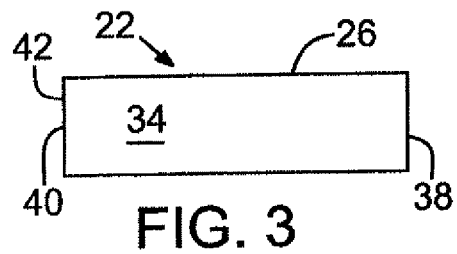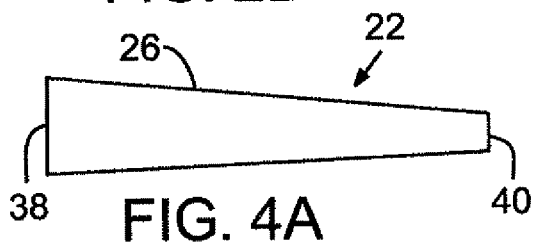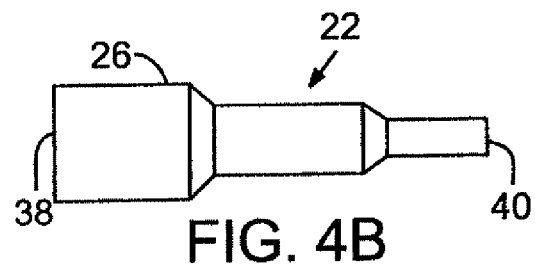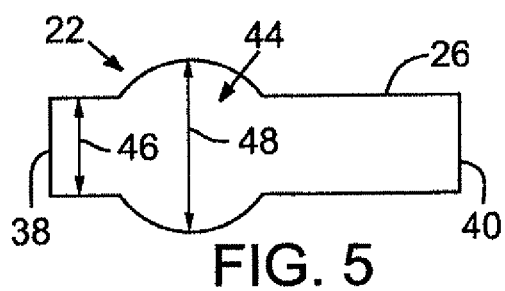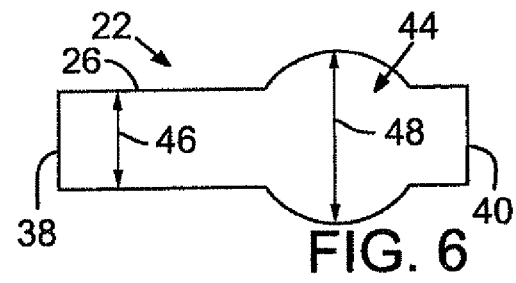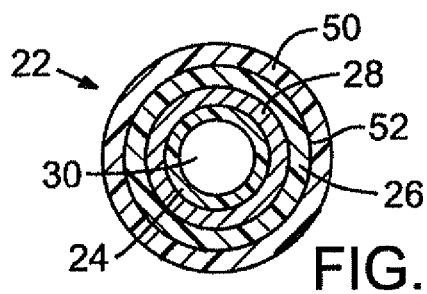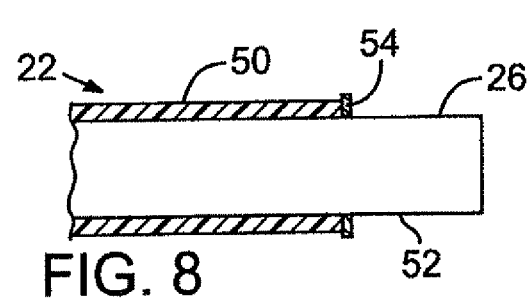

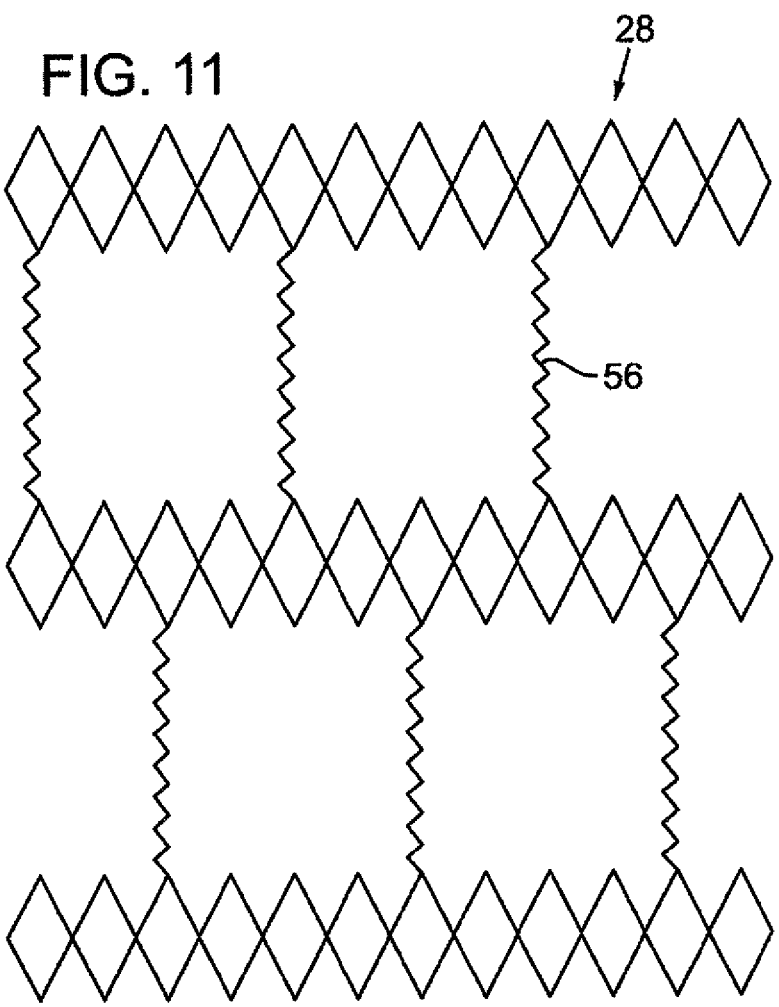

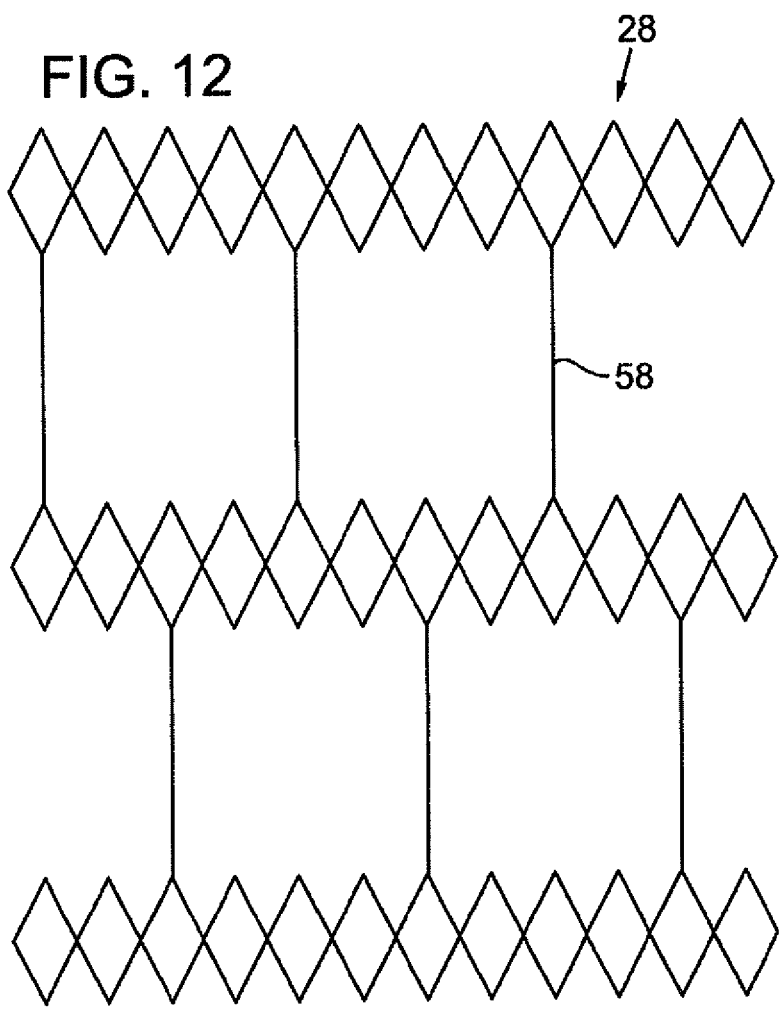

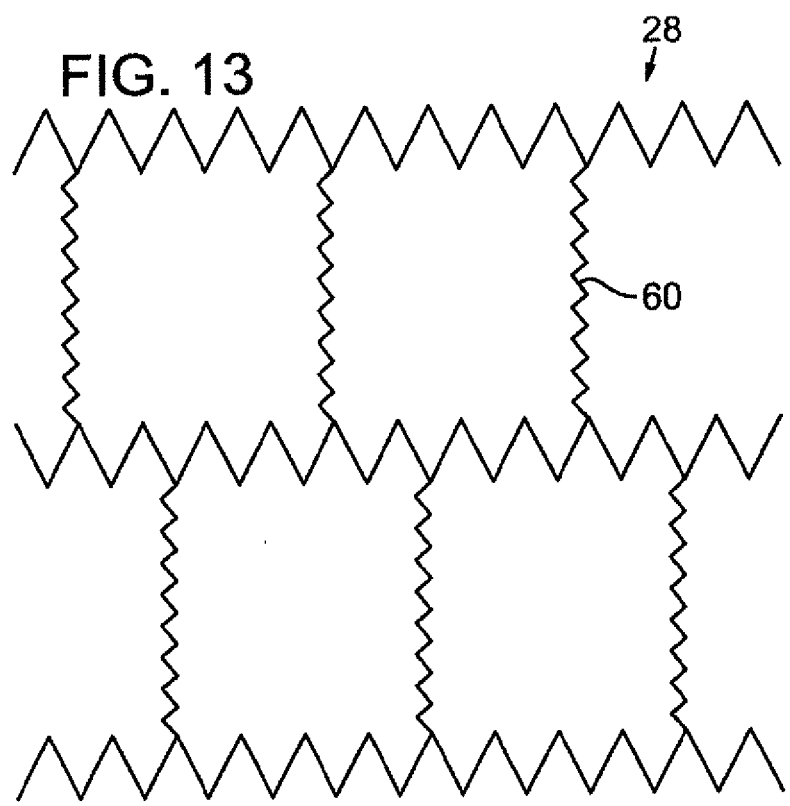
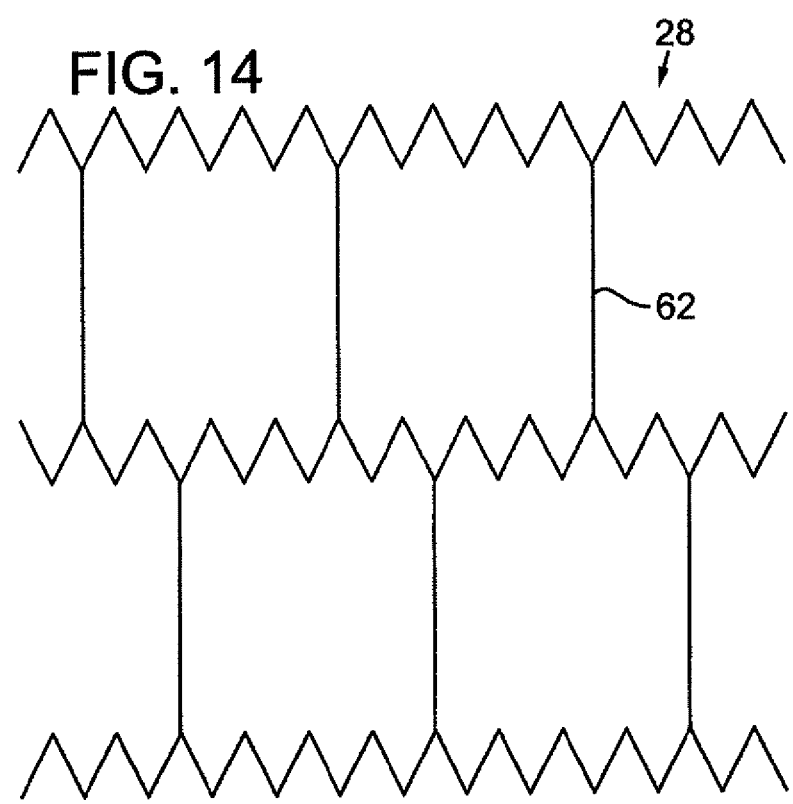

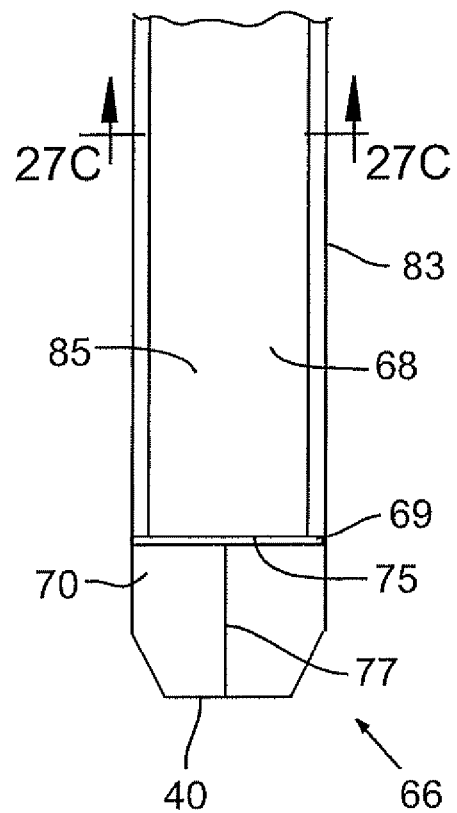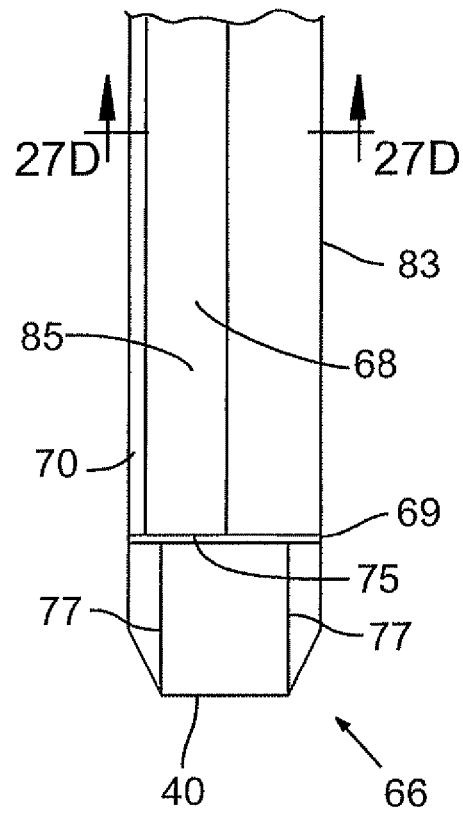

EXPANDABLE SHEATH FOR INTRODUCING AN ENDOVASCULAR DELIVERY DEVICE INTO A BODY

FIELD

The present application concerns embodiments of a sheath for use with catheter-based technologies for repairing and/or replacing heart valves, as well as for delivering a prosthetic device, such as a prosthetic valve to a heart via the patient's vasculature.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a significant risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

Accordingly, there remains a need in the art for an improved introducer sheath for endovascular systems used for implanting valves and other prosthetic devices.

SUMMARY

Embodiments of the present expandable sheath can minimize trauma to the vessel by allowing for temporary expansion of a portion of the introducer sheath to accommodate a delivery system, followed by a return to the original diameter once the delivery system passes through. Some embodiments can comprise a sheath with a smaller profile than that of prior art introducer sheaths. Furthermore, certain embodiments can reduce the length of time a procedure takes, as well as reduce the risk of a longitudinal or radial vessel tear, or plaque dislodgement because only one sheath is required, rather than several different sizes of sheaths. Embodiments of the present expandable sheath can require only a single vessel insertion, as opposed to requiring multiple insertions for the dilation of the vessel.

One embodiment of a sheath for introducing a prosthetic device comprises an inner tubular layer, an outer tubular layer, and an intermediate tubular layer disposed between the inner and outer tubular layers. At least a portion of the sheath can be designed or configured to locally expand from a first diameter to a second diameter as the prosthetic device is pushed through a lumen of the sheath, and then at least partially return to the first diameter once the prosthetic device has passed through.

The inner tubular layer can comprise polytetrafluoroethylene (PTFE), polyimide, polyetheretherketone (PEEK), polyurethane, nylon, polyethylene, polyamide, or combinations thereof. The intermediate tubular layer can comprise Nitinol, stainless steel, cobalt chromium, spectra fiber, polyethylene fiber, aramid fiber, or combinations thereof. The outer tubular layer can comprise PTFE, polyimide, PEEK, polyurethane, nylon, polyethylene, polyamide, polyether block amides, polyether block ester copolymer, thermoset silicone, latex, poly-isoprene rubbers, or combinations thereof.

Disclosed embodiments of a sheath comprise a proximal and a distal end opposite one another, and a hemostasis valve at or near the proximal end of the sheath. In some embodiments, the outer diameter of the sheath decreases along a gradient from the proximal end to the distal end of the sheath.

Some embodiments of a sheath for introducing a prosthetic device comprise an outer tubular layer, at least a portion of which is adapted to split along its length as the prosthetic device passes through the lumen to facilitate expansion of the sheath. Alternatively, or in addition to, some embodiments of a sheath comprise an inner tubular layer, at least a portion of which is adapted to split along its length as the prosthetic device passes through the lumen to facilitate radial expansion of the sheath. In some embodiments, the inner tubular layer and/or the outer tubular layer comprises a longitudinal cut or notch along at least a portion of its length.

Disclosed embodiments of a sheath for introducing a prosthetic device comprise an outer covering disposed on the outer surface of the outer tubular layer. In some embodiments, the outer covering is removable and/or adapted to split along at least a portion of its length to facilitate radial expansion of the sheath. For example, the outer covering can be provided with peel tabs to facilitate splitting and/or sliding the outer covering off of the underlying sheath once a portion of the sheath is inserted into a patient's vessel.

The intermediate tubular layer is discontinuous in some embodiments. For example, the intermediate tubular layer can comprise a mesh structure having at least two sections spaced apart from each other along a longitudinal axis parallel to the lumen of the sheath. In such embodiments, each section can be connected by at least one strut to an adjacent section. Similarly, embodiments of a sheath can comprise an inner tubular layer with at least one discontinuous section along its longitudinal axis to facilitate radial expansion of the inner tubular layer. In some embodiments, the intermediate layer is self-expandable.

Additionally, disclosed embodiments can further comprise a lubricating liner on at least a portion of the inner surface of the inner tubular layer and/or an exterior hydrophilic coating on at least a portion of the outer surface of the outer tubular layer. Sheaths can also comprise at least one radiopaque filler and/or marker, such as barium sulfite, bismuth trioxide, titanium dioxide, bismuth subcarbonate, or combinations thereof.

Some embodiments of a sheath for introducing a prosthetic device into a patient's vasculature comprise an inner tubular layer, an outer covering, and a self-expanding intermediate tubular layer disposed between the inner tubular layer and the outer covering. The outer covering can be adapted to maintain the self-expanding intermediate tubular layer in a crimped state having a first diameter, wherein the outer covering is at least partially moveable along the length of the sheath or removable from the sheath once the sheath is at least partially inserted into the patient's vasculature, to allow for self-expansion of the intermediate tubular layer to an expanded state having a second diameter greater than the first diameter. In some embodiments, the sheath is adapted to at least partially compress towards the first diameter upon removal of the sheath from the patient's vasculature. To facilitate moving or removing the outer covering from the sheath, some embodiments comprise an outer covering provided with at least one peel tab.

Some embodiments of a sheath comprise an inner tubular layer and an outer tubular layer, where the outer tubular layer includes at least one longitudinal cut through it such that the outer tubular layer comprises a first longitudinal edge, a second longitudinal edge, and a gap there between, wherein the inner tubular layer is associated with an inner surface of the outer tubular layer, and wherein a portion of the inner tubular layer extends through the gap.

In some embodiments, the portion of the inner tubular layer that extends through the gap forms a folded portion outside the outer tubular layer.

Some embodiments of a sheath also comprise an outer covering over at least a portion of an outer surface of the outer tubular layer, wherein the outer covering overlaps at least a portion of the folded portion of the inner tubular layer.

At least a portion of an outer surface of the inner tubular layer can be surface treated, etched, or otherwise modified. The inner tubular layer and the outer tubular layer can be adhesively secured to each other substantially only at the portion that is surface treated or etched, so as to substantially avoid interference with radial expansion of the sheath.

In some embodiments, the inner tubular layer comprises PTFE. In some embodiments, the outer tubular layer comprises high density polyethylene.

Methods of making a sheath are also disclosed. One method comprises providing a mandrel, mounting an inner layer on the mandrel such that the mandrel is positioned within a lumen formed by the inner layer, mounting an outer layer having a longitudinal cut on the inner layer such that an excess portion of the inner layer extends through the longitudinal cut, and forming a pleat or fold in the excess portion of the inner layer.

Another method of making a sheath comprises providing a mandrel and applying an inner layer on the mandrel, such as by spray coating or dip coating the mandrel. An intermediate layer can then be mounted on the inner layer. An outer layer can be applied over the intermediate layer, such as by a second spray coating or dip coating step.

Methods can comprise etching or surface treating at least a portion of the inner layer.

In some embodiments of methods of making a sheath, layers can be pre-formed and mounted on a mandrel, and then fused or thermally bonded together. For example, in one method, an inner layer is applied to a mandrel. An intermediate layer can be applied to the outer surface of the inner layer. An outer layer can be applied to the outer surface of the intermediate layer. Heat shrink tubing can be applied, and the assembly heated, such that the inner layer, the intermediate layer, and/or the outer layer are thermally bonded and compressed together under the heat shrink tubing.

In some embodiments of a method of making a sheath, a second mandrel is provided. The second mandrel can be inserted within a second lumen formed by the excess portion of the inner layer.

Methods of making a sheath can comprise applying a radiopaque marker and/or filler to the inner and/or outer layer of the sheath, or embedding such markers and/or fillers within one or more of the inner and outer layers of the sheath.

In some methods, a partial slit or score line can be applied to the sheath. For example, a partial slit or score line can be cut in the sheath such that the score line extends from a point distal to a radiopaque marker to the distal tip of the sheath.

A sheath can also be provided with an over covering in some methods. The outer covering can be associated with an outer surface of the outer layer, such that at least a portion of the outer covering overlaps at least a portion of the pleat or fold formed in the excess portion of the inner portion extending through the longitudinal cut in the outer layer.

Disclosed methods of introducing a prosthetic device into a patient's vasculature comprise positioning a expandable introducer sheath in a patient's vessel, wherein the expandable introducer sheath comprises an inner tubular layer and an outer tubular layer, wherein the outer tubular layer contains a longitudinal cut through it such that the outer tubular layer comprises a first longitudinal edge, a second longitudinal edge, and a gap there between, and wherein a portion of the inner tubular layer extends through the gap, introducing the device into the expandable introducer sheath, expanding a portion of the introducer sheath via radial force applied by the device at the location of the expanded portion, moving the device through the expanded portion, and at least partially collapsing the expanded portion of the introducer sheath after the device has passed through the expanded portion.

The foregoing and other features and advantages of the invention will become more apparent from the following detailed description, which proceeds with reference to the accompanying figures.

BRIEF DESCRIPTION OF THE DRAWINGS

FIGS. 2A, B, and D are section views of embodiments of a sheath for introducing a prosthetic device into a patient, and FIG. 2C is a perspective view of one component of such a sheath.

FIG. 3 is an elevation view of the sheath shown in FIG. 2.

FIGS. 4A-4B are elevation views of two embodiments of a sheath according to the present disclosure, having varying outer diameters.

FIG. 5 illustrates an elevation view of one embodiment of a sheath, expanded at a first location to accommodate a delivery system.

FIG. 6 shows an elevation view of the sheath of claim 5, expanded at a second location, farther down the sheath.

FIG. 7 shows a section view of another embodiment of a sheath that further comprises an outer covering or shell.

FIG. 8 illustrates an elevation view of one embodiment of a sheath with an outer covering or shell.

FIG. 11 illustrates a partial elevation view of another embodiment of an intermediate tubular layer having a diamond design with spring struts.

FIG. 12 illustrates a partial elevation view of another embodiment of an intermediate tubular layer having a diamond design with straight struts.

FIG. 13 illustrates a partial elevation view of another embodiment of an intermediate tubular layer having a saw tooth design with spring struts.

FIG. 14 illustrates a partial elevation view of another embodiment of an intermediate tubular layer having a saw tooth design with straight struts.

FIG. 33 illustrates a plan view of one embodiment of a sheath having a partial slit or score line.

FIG. 34 illustrates a plan view of another embodiment of a sheath having a partial slit or score line.

DETAILED DESCRIPTION

As used in this application and in the claims, the singular forms "a," "an," and "the" include the plural forms unless the context clearly dictates otherwise. Additionally, the term "includes" means "comprises." Further, the terms "coupled" and "associated" generally means electrically, electromagnetically, and/or physically (e.g., mechanically or chemically) coupled or linked and does not exclude the presence of intermediate elements between the coupled or associated items.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Disclosed embodiments of an expandable sheath can minimize trauma to the vessel by allowing for temporary expansion of a portion of the introducer sheath to accommodate the delivery system, followed by a return to the original diameter once the device passes through. Some embodiments can comprise a sheath with a smaller profile than that of prior art introducer sheaths. Furthermore, present embodiments can reduce the length of time a procedure takes, as well as reduce the risk of a longitudinal or radial vessel tear, or plaque dislodgement because only one sheath is required, rather than several different sizes of sheaths. Embodiments of the present expandable sheath can avoid the need for multiple insertions for the dilation of the vessel.

Figure 1:
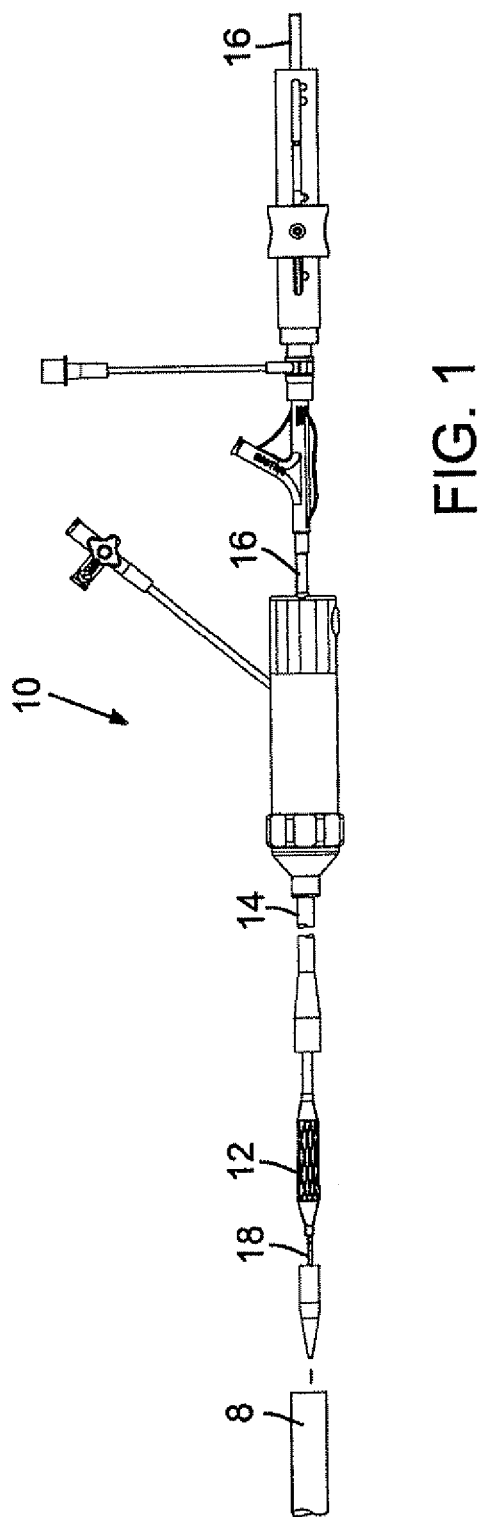
FIG. 1 is an elevation view of a sheath according to the present disclosure along with an endovascular delivery apparatus for implanting a prosthetic valve.
Figure 9:
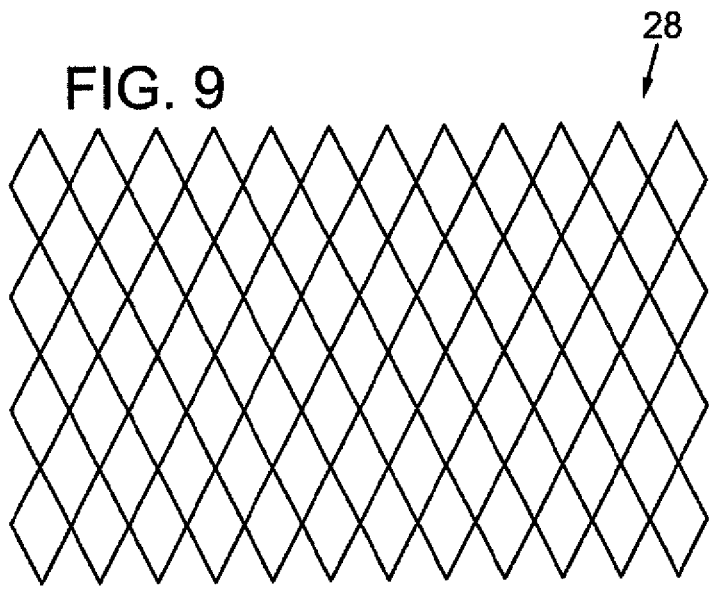
FIG. 9 illustrates a partial elevation view of one embodiment of an intermediate tubular layer that can be used to construct a sheath according to the present disclosure.
Figure 10:
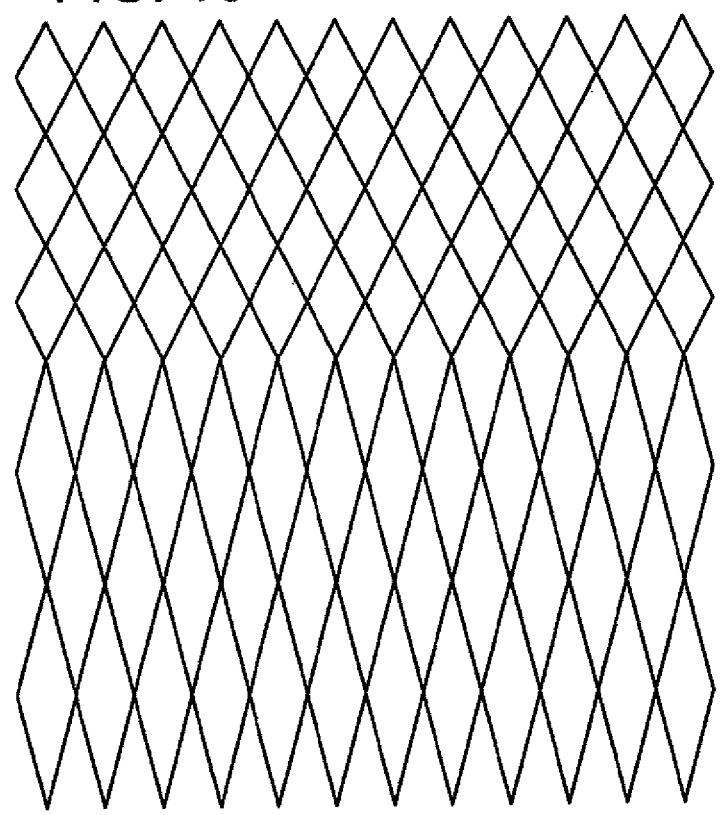
FIG. 10 illustrates a partial elevation view of another embodiment of an intermediate tubular layer having a variable diamond design.
Figure 15:
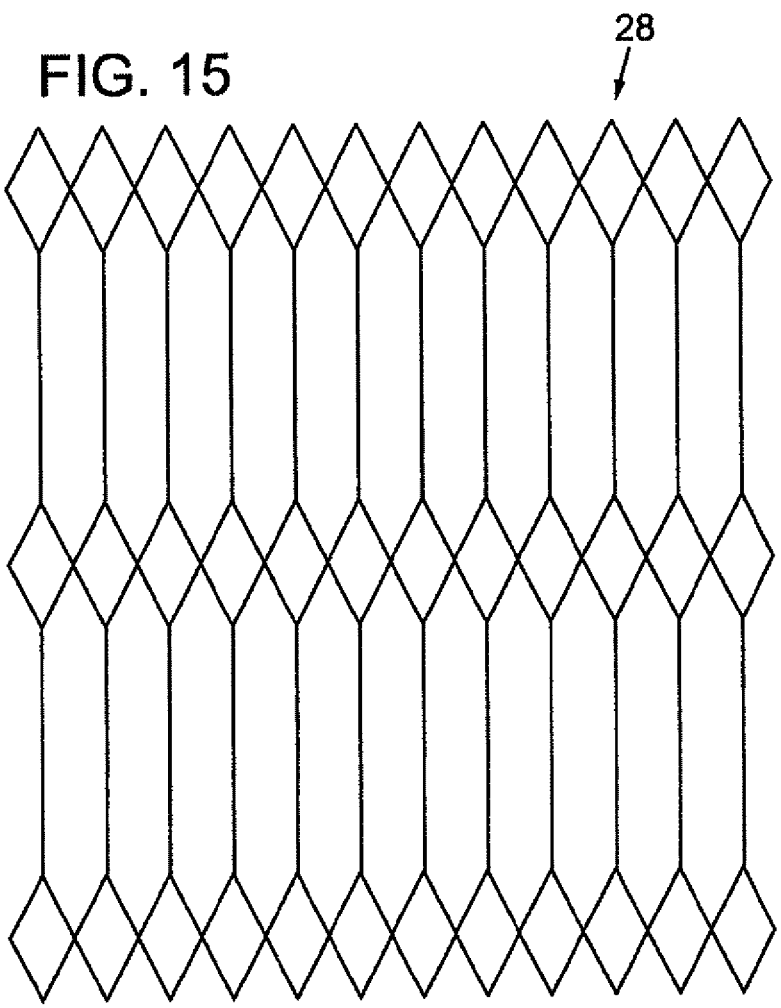
FIG. 15 illustrates a partial elevation view of another embodiment of an intermediate tubular layer having a diamond design with straight struts.
Figure 16:
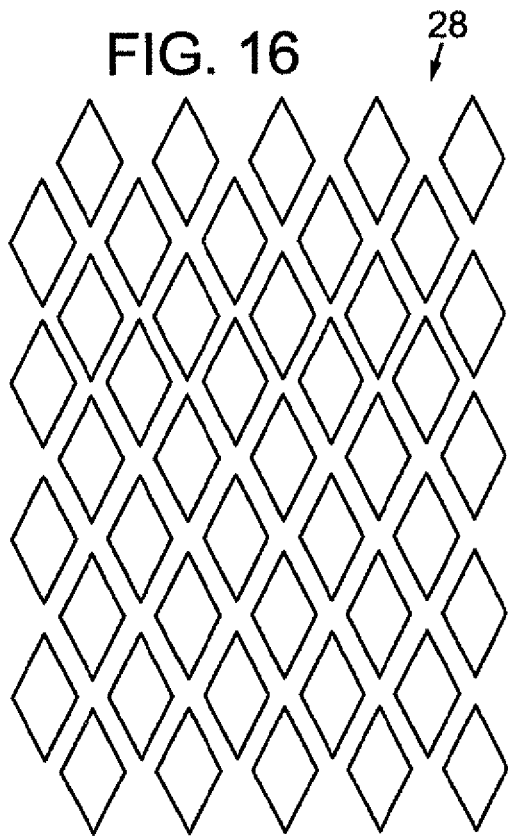
FIG. 16 illustrates a partial elevation view of another embodiment of an intermediate tubular layer having a helical or spiral design.
Figure 17:
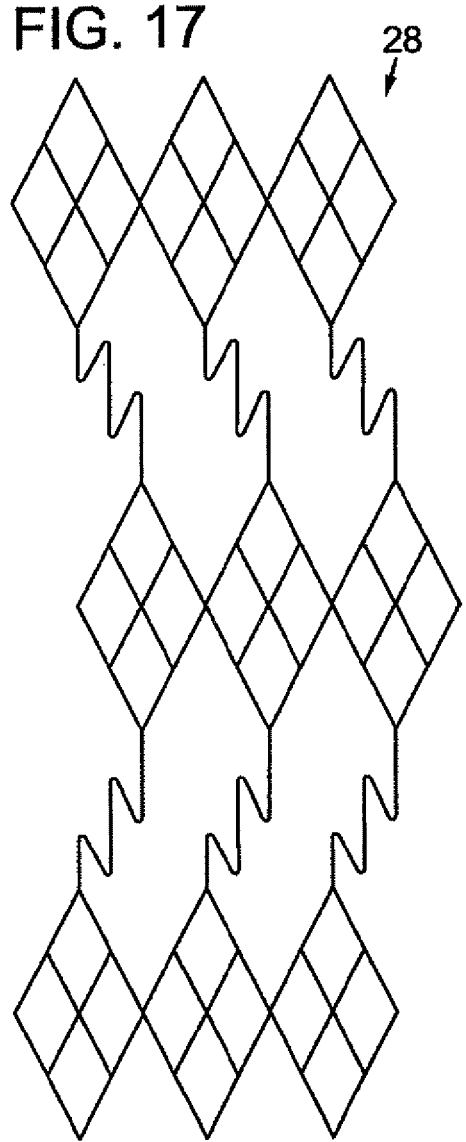
FIG. 17 illustrates a partial elevation view of another embodiment of an intermediate tubular layer having a diamond design with non-straight struts.
Figure 18:
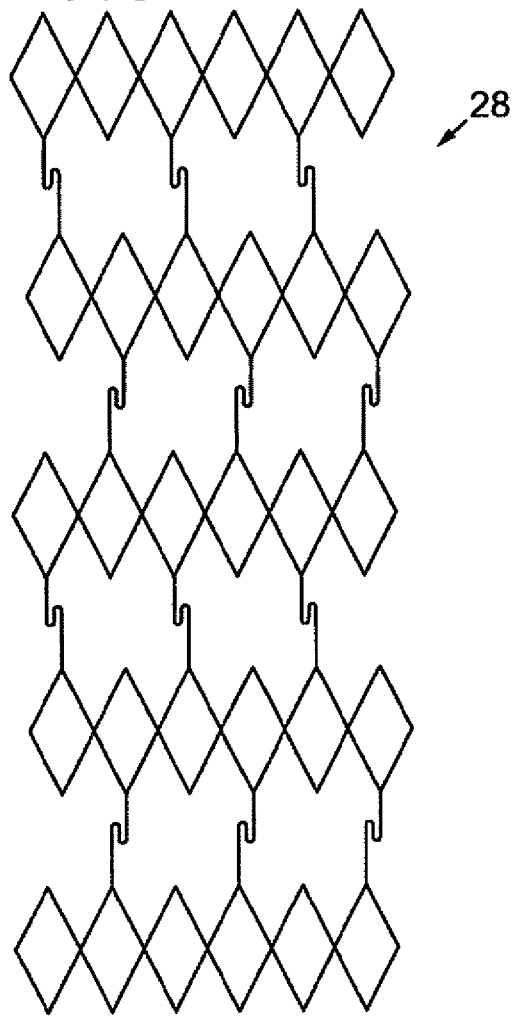
FIG. 18 illustrates a partial elevation view of another embodiment of an intermediate tubular layer having an alternative diamond design with non-straight struts.
Figure 19:
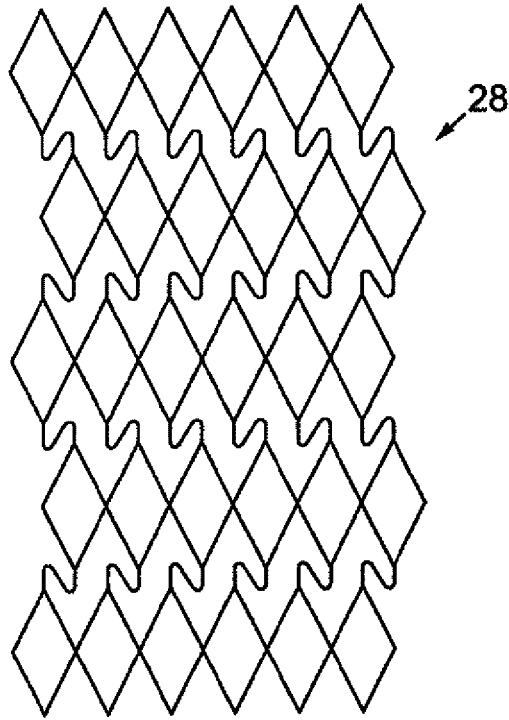
FIG. 19 illustrates a partial elevation view of another embodiment of an intermediate tubular layer having yet another diamond design with non-straight struts.
Figure 20:
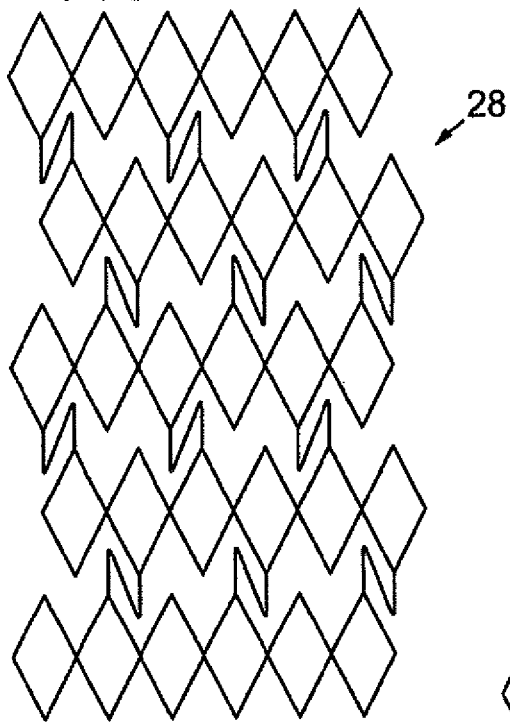
FIG. 20 illustrates a partial elevation view of another embodiment of an intermediate tubular layer having a diamond design with struts.
Figure 21:
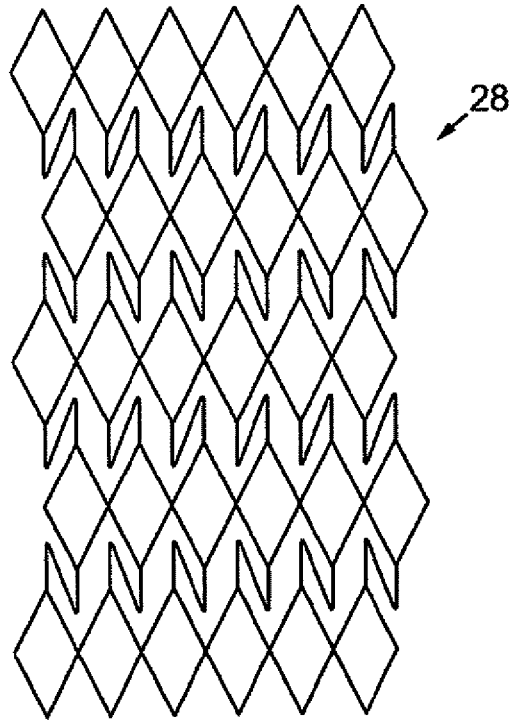
FIG. 21 illustrates a partial elevation view of another embodiment of an intermediate tubular layer having a design similar to that shown in FIG. 20, but with additional struts.
Figure 22:
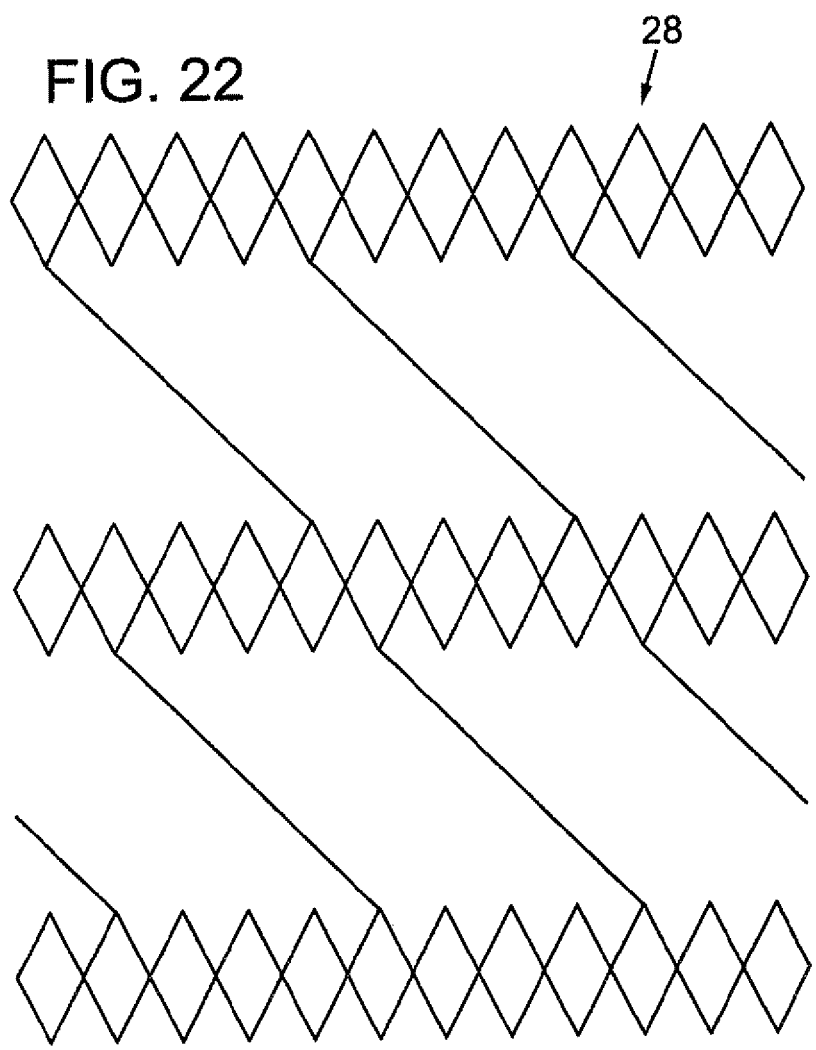
FIG. 22 illustrates a partial elevation view of another embodiment of an intermediate tubular layer having a diamond design with spiral struts.
Figure 23:
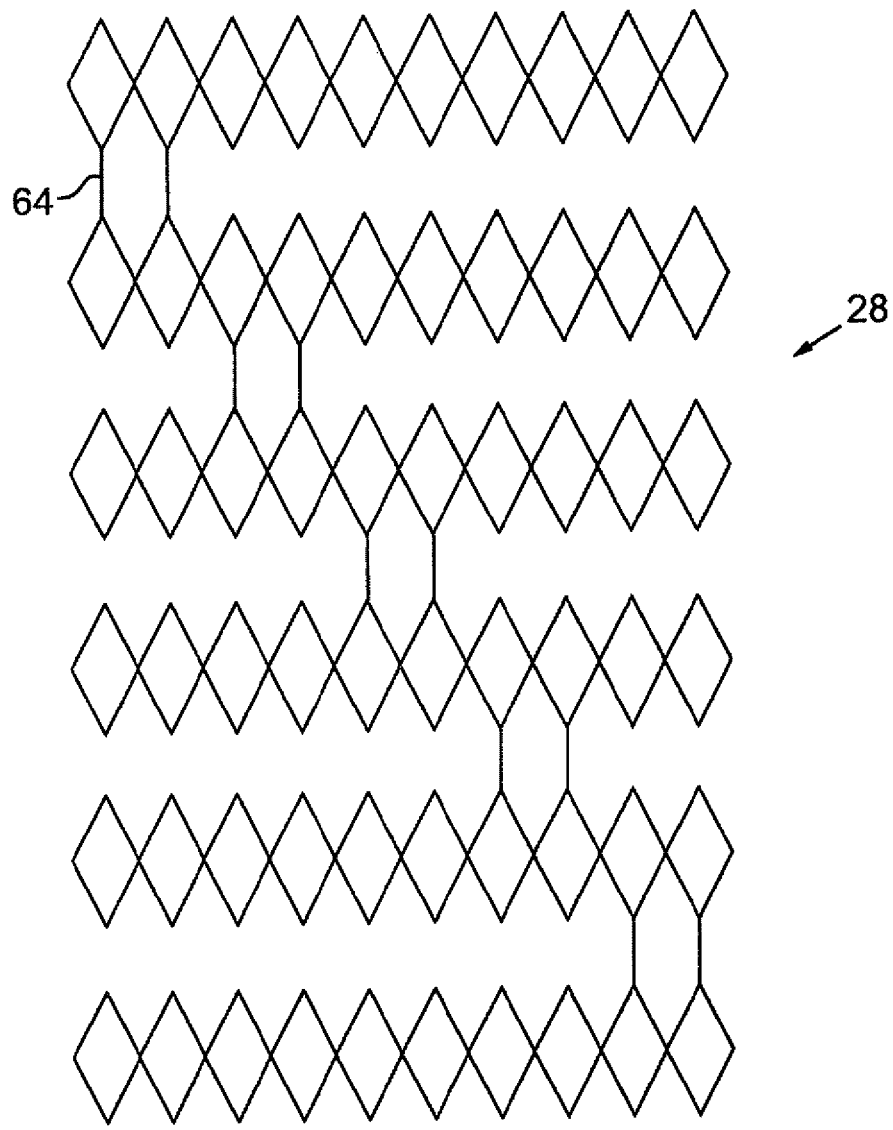
FIG. 23 illustrates a partial elevation view of another embodiment of an intermediate tubular layer having a diamond design with adjacent struts.

FIG. 1 illustrates a sheath 8 according to the present disclosure, in use with a representative delivery apparatus 10, for delivering a prosthetic device 12, such as a tissue heart valve to a patient. The apparatus 10 can include a steerable guide catheter 14 (also referred to as a flex catheter), a balloon catheter 16 extending through the guide catheter 14, and a nose catheter 18 extending through the balloon catheter 16. The guide catheter 14, the balloon catheter 16, and the nose catheter 18 in the illustrated embodiment are adapted to slide longitudinally relative to each other to facilitate delivery and positioning of the valve 12 at an implantation site in a patient's body, as described in detail below. Generally, sheath 8 is inserted into a vessel, such as the transfemoral vessel, passing through the skin of patient, such that the distal end of the sheath 8 is inserted into the vessel. Sheath 8 can include a hemostasis valve at the opposite, proximal end of the sheath.

The delivery apparatus 10 can be inserted into the sheath 8, and the prosthetic device 12 can then be delivered and implanted within patient.

FIGS. 2A, 2B, and 2D show section views of embodiments of a sheath 22 for use with a delivery apparatus such as that shown in FIG. 1. FIG. 2C shows a perspective view of one embodiment of an inner layer 24 for use with the sheath 22. Sheath 22 includes an inner layer, such as inner polymeric tubular layer 24, an outer layer, such as outer polymeric tubular layer 26, and an intermediate tubular layer 28 disposed between the inner and outer polymeric tubular layers 24, 26. The sheath 22 defines a lumen 30 through which a delivery apparatus can travel into a patient's vessel in order to deliver, remove, repair, and/or replace a prosthetic device. Such introducer sheaths 22 can also be useful for other types of minimally invasive surgery, such as any surgery requiring introduction of an apparatus into a subject's vessel. For example, the sheath 22 also can be used to introduce other types of delivery apparatus for placing various types of intraluminal devices (e.g., stents, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

The outer polymeric tubular layer 26 and the inner polymeric tubular layer 24 can comprise, for example, PTFE (e.g. Teflon®), polyimide, PEEK, polyurethane, nylon, polyethylene, polyamide, polyether block amides (e.g. PEBAX®), polyether block ester copolymer, polyesters, fluoropolymers, polyvinyl chloride, thermoset silicone, latex, poly-isoprene rubbers, polyolefin, other medical grade polymers, or combinations thereof. The intermediate tubular layer 28 can comprise a shape memory alloy such as Nitinol, and/or stainless steel, cobalt chromium, spectra fiber, polyethylene fiber, aramid fiber, or combinations thereof.

The inner polymeric tubular layer 24 can advantageously be provided with a low coefficient of friction on its inner surface. For example, the inner polymeric tubular layer 24 can have a coefficient of friction of less than about 0.1. Some embodiments of a sheath 22 can include a lubricious liner on the inner surface 32 of the inner polymeric tubular layer 24. Such a liner can facilitate passage of a delivery apparatus through the lumen 30 of the sheath 22. Examples of suitable lubricious liners include materials that can reduce the coefficient of friction of the inner polymeric tubular layer 24, such as PTFE, polyethylene, polyvinylidine fluoride, and combinations thereof. Suitable materials for a lubricious liner also include other materials desirably having a coefficient of friction of about 0.1 or less.

The inner diameter of the intermediate tubular layer 28 varies depending on the application and size of the delivery apparatus and prosthetic device. In some embodiments, the inner diameter ranges from about 0.005 inches to about 0.400 inches. The thickness of the intermediate tubular layer 28 can be varied depending on the desired amount of radial expansion, as well as the strength required. For example, the thickness of the intermediate tubular layer 28 can be from about 0.002 inches to about 0.025 inches. The thicknesses of the inner polymeric tubular layer 24 and the outer polymeric tubular layer 26 can also be varied depending on the particular application of the sheath 22. In some embodiments, the thickness of the inner polymeric tubular layer 24 ranges from about 0.0005 inches to about 0.010 inches, and in one particular embodiment, the thickness is about 0.002 inches. Outer polymeric tubular layers 26 can have a thickness of from about 0.002 inches to about 0.015 inches, and in one particular embodiment the outer polymeric tubular layer 26 has a thickness of about 0.010 inches.

The hardness of each layer of the sheath 22 can also be varied depending on the particular application and desired properties of the sheath 22. In some embodiments, the outer polymeric tubular layer 26 has a Shore hardness of from about 25 Durometer to about 75 Durometer.

Additionally, some embodiments of a sheath 22 can include an exterior hydrophilic coating on the outer surface 34 of the outer polymeric tubular layer 26. Such a hydrophilic coating can facilitate insertion of the sheath 22 into a patient's vessel. Examples of suitable hydrophilic coatings include the Harmony™ Advanced Lubricity Coatings and other Advanced Hydrophilic Coatings available from SurModics, Inc., Eden Prairie, Minn. DSM medical coatings (available from Koninklijke DSM N.V, Heerlen, the Netherlands), as well as other hydrophilic coatings, are also suitable for use with the sheath 22.

In some embodiments, the outer surface 34 of the outer polymeric tubular layer 26 can be modified. For example, surface modifications such as plasma etching can be performed on the outer surface 34. Similarly, other surfaces, both outer and inner, can be surface modified according to certain embodiments and desired application. In some embodiments, surface modification can improve adhesion between the layers in the areas of the modification.

The sheath 22 also can have at least one radiopaque filler or marker. The radiopaque filler or marker can be associated with the outer surface 34 of the outer polymeric tubular layer 26. Alternatively, the radiopaque filler or marker can be embedded or blended within the outer polymeric tubular layer 24. Similarly, the radiopaque filler or marker can be associated with a surface of the inner polymeric tubular layer 24 or the intermediate tubular layer 28 or embedded within either or both of those layers.

Suitable materials for use as a radiopaque filler or marker include, for example, barium sulfite, bismuth trioxide, titanium dioxide, bismuth subcarbonate, or combinations thereof. The radiopaque filler can be mixed with or embedded in the material used to form the outer polymeric tubular layer 26, and can comprise from about 5% to about 45% by weight of the outer polymeric tubular layer. More or less radiopaque material can be used in some embodiments, depending on the particular application.

In some embodiments, the inner polymeric tubular layer 24 can comprise a substantially uniform cylindrical tube. In alternative embodiments, the inner polymeric tubular layer 24 can have at least one section of discontinuity along its longitudinal axis to facilitate radial expansion of the inner polymeric tubular layer 24. For example, the inner polymeric tubular layer 24 can be provided with one or more longitudinal notches and/or cuts 36 extending along at least a portion of the length of the sheath 22. Such notches or cuts 36 can facilitate radial expansion of the inner polymeric tubular layer 24, thus accommodating passage of a delivery apparatus or other device. Such notches and/or cuts 36 can be provided near the inner surface 32, near the outer surface 37, and/or substantially through the entire thickness of the inner polymeric layer 24. In embodiments with a plurality of notches and/or cuts 36, such notches and/or cuts 36 can be positioned such that they are substantially equally spaced from one another circumferentially around the inner polymeric layer 24. Alternatively, notches and cuts 36 can be spaced randomly in relation to one another, or in any other desired pattern. Some or all of any provided notches and/or cuts 36 can extend longitudinally along substantially the entire length of the sheath 22. Alternatively, some or all of any provided notches and/or cuts 36 can extend longitudinally only along a portion of the length of the sheath 22.

As shown in FIGS. 2B and 2C (which illustrates only the inner polymeric tubular layer 24), in some embodiments, the inner polymeric tubular layer 24 contains at least one notch or cut 36 that extends longitudinally and parallel to an axis defined by the lumen 30, extending substantially the entire length of the sheath 22. Thus, upon introduction of a delivery apparatus, the inner polymeric tubular layer 24 can split open along the notch and/or cut 36 and expand, thus accommodating the delivery apparatus.

Additionally or alternatively, as shown in FIG. 2D, the outer polymeric tubular layer 26 can comprise one or more notches and/or cuts 36. Notches and/or cuts 36, in some embodiments, do not extend through the entire thickness of the outer tubular layer 26. The notches and/or cuts 36 can be separable upon radial expansion of the sheath 22. The outer polymeric tubular layer 26 can be retractable longitudinally, or able to be pulled back away from the intermediate tubular layer 28 and the inner polymeric tubular layer 24. In embodiments with a retractable outer polymeric tubular layer 26, the outer polymeric tubular layer 26 can be retracted to accommodate or facilitate passage of a delivery apparatus through the lumen 30, and then can be replaced to its original position on the sheath 22.

FIG. 3 illustrates an elevation view of the sheath 22 shown in FIG. 2A. In this view, only the outer polymeric tubular layer 26 is visible. The sheath 22 comprises a proximal end 38 and a distal end 40 opposite the proximal end 38. The sheath 22 can include a hemostasis valve inside the lumen of the sheath 22, at or near the proximal end 38 of the sheath 22. Additionally, the sheath 22 can comprise a soft tip 42 at the distal end 40 of the sheath 22. Such a soft tip 42 can be provided with a lower hardness than the other portions of the sheath 22. In some embodiments, the soft tip 42 can have a Shore hardness from about 25 D to about 40 D.

As shown in FIG. 3, the unexpanded original outer diameter of the sheath 22 can be substantially constant across the length of the sheath 22, substantially from the proximal end 38 to the distal end 40. In alternative embodiments, such as the ones illustrated in FIGS. 4A-4B, the original unexpanded outer diameter of the sheath 22 can decrease from the proximal end 38 to the distal end 40. As shown in the embodiment in FIG. 4A, the original unexpanded outer diameter can decrease along a gradient, from the proximal end 38 to the distal end 40. In alternative embodiments, such as the one shown in FIG. 4B, the original unexpanded outer diameter of sheath 22 can incrementally step down along the length of the sheath 22, wherein the largest original unexpanded outer diameter is near the proximal end 38 and the smallest original unexpanded outer diameter is near the distal end 40 of the sheath 22.

As shown in FIGS. 5-6, the sheath 22 can be designed to locally expand as the prosthetic device is passed through the lumen of the sheath 22, and then substantially return to its original shape once the prosthetic device has passed through that portion of the sheath 22. For example, FIG. 5 illustrates a sheath 22 have a localized bulge 44, representative of a device being passed through the internal lumen of the sheath 22. FIG. 5 shows the device close to the proximal end 38 of the sheath 22, close to the area where the device is introduced into the sheath 22. FIG. 6 shows the sheath 22 of FIG. 5, with the device having progressed further along the sheath 22. The localized bulge 44 is now closer to the distal end 40 of the sheath 22, and thus is about to be introduced to a patient's vessel. As evident from FIGS. 5 and 6, once the localized bulge associated with the device has passed through a portion of the lumen of the sheath 22, that portion of the sheath 22 can automatically return to its original shape and size, at least in part due to the materials and structure of the sheath 22.

The sheath 22 has an unexpanded inner diameter equal to the inner diameter of the inner polymeric tubular layer (not visible in FIGS. 5-6), and an unexpanded outer diameter 46 equal to the outer diameter of the outer polymeric tubular layer 26. The sheath 22 is designed to be expanded to an expanded inner diameter and an expanded outer diameter 48 which are larger than the unexpanded inner diameter and the unexpanded outer diameter 46, respectively. In one representative embodiment, the unexpanded inner diameter is about 16 Fr and the unexpanded outer diameter 46 is about 19 Fr, while the expanded inner diameter is about 26 Fr and the expanded outer diameter 48 is about 29 Fr. Different sheaths 22 can be provided with different expanded and unexpanded inner and outer diameters, depending on the size requirements of the delivery apparatus for various applications. Additionally, some embodiments can provide more or less expansion depending on the particular design parameters, the materials, and/or configurations used.

In some embodiments of a sheath according to the present disclosure, and as shown in section in FIG. 7 and in elevation in FIG. 8, the sheath 22 can additionally comprise an outer covering, such as outer polymeric covering 50, disposed on the outer surface 52 of the outer polymeric tubular layer 26. The outer polymeric covering 50 can provide a protective covering for the underlying sheath 22. In some embodiments, the outer polymeric covering 50 can contain a self-expandable sheath in a crimped or constrained state, and then release the self-expandable sheath upon removal of the outer polymeric covering 50. For example, in some embodiments of a self-expandable sheath, the intermediate layer 28 can comprise Nitinol and/or other shape memory alloys, and the intermediate layer 28 can be crimped or radially compressed to a reduced diameter within the outer polymeric tubular layer 26 and the outer polymeric covering 50. Once the self-expandable sheath is at least partially inserted into a patient's vessel, the outer polymeric covering 50 can be slid back, peeled away, or otherwise at least partially removed from the sheath. To facilitate removal of the outer polymeric covering 50, a portion of the outer polymeric covering 50 can remain outside the patient's vessel, and that portion can be pulled back or removed from the sheath to allow the sheath to expand. In some embodiments, substantially the entire outer polymeric covering 50 can be inserted, along with the sheath, into a patient's vessel. In these embodiments, an external mechanism attached to the outer polymeric covering 50 can be provided, such that the outer polymeric covering can be at least partially removed from the sheath once the sheath is inserted into a patient's vessel.

Once no longer constrained by the outer polymeric covering 50, the radially compressed intermediate layer 28 can self-expand, causing expansion of the sheath along the length of the intermediate layer 28. In some embodiments, portions of the sheath can radially collapse, at least partially returning to the original crimped state, as the sheath is being withdrawn from the vessel after completion of the surgical procedure. In some embodiments, such collapse can be facilitated and/or encouraged by an additional device or layer that, in some embodiments, can be mounted onto a portion of the sheath prior to the sheath's insertion into the vessel.

The outer polymeric covering 50, in some embodiments, is not adhered to the other layers of the sheath 22. For example, the outer polymeric covering 50 may be slidable with respect to the underlying sheath, such that it can be easily removed or retracted from its initial position on the sheath 22.

As seen in FIG. 8, the outer polymeric covering 50 can include one or more peel tabs 54 to facilitate manual removal of the outer polymeric covering 50. The outer polymeric covering 50 can be automatically or manually retractable and/or splittable to facilitate radial expansion of the sheath 22. Peel tabs 54 can be located approximately 90 degrees from any cut or notch present in the outer polymeric covering 50, and approximately 180 degrees offset from one another. In alternative embodiments, the peel tabs 54 can extend substantially around the circumference of the outer polymeric covering 50, thus resulting in a single circular peel tab 54.

Suitable materials for the outer polymeric covering 50 are similar to those materials suitable for the inner polymeric tubular layer and the outer polymeric tubular layer, and can include PTFE and/or high density polyethylene.

Turning now to the intermediate tubular layer 28, several different configurations are possible. The intermediate tubular layer 28 is generally a thin, hollow, substantially cylindrical tube comprising an arrangement, pattern, structure, or configuration of wires or struts, however other geometries can also be used. The intermediate tubular layer 28 can extend along substantially the entire length of the sheath 22, or alternatively, can extend only along a portion of the length of sheath 22. Suitable wires can be round, ranging from about 0.0005 inches thick to about 0.10 inches thick, or flat, ranging from about 0.0005 inches×0.003 inches to about 0.003 inches×0.007 inches. However, other geometries and sizes are also suitable for certain embodiments. If braided wire is used, the braid density can be varied. Some embodiments have a braid density of from about thirty picks per inch to about eighty picks per inch and can include up to thirty-two wires in various braid patterns.

One representative embodiment of an intermediate tubular layer comprises a braided Nitinol composite which is at least partially encapsulated by an inner polymeric tubular member and an outer polymeric tubular member disposed on inner and outer surfaces of the intermediate tubular layer, respectively. Such encapsulation by polymeric layers can be accomplished by, for example, fusing the polymeric layers to the intermediate tubular layer, or dip coating the intermediate tubular layer. In some embodiments, an inner polymeric tubular member, an intermediate tubular layer, and an outer polymeric tubular layer can be arranged on a mandrel, and the layers can then be thermally fused or melted into one another by placing the assembly in an oven or otherwise heating it. The mandrel can then be removed from the resulting sheath. In other embodiments, dip coating can be used to apply an inner polymeric tubular member to the surface of a mandrel. The intermediate tubular layer can then be applied, and the inner polymeric tubular member allowed to cure. The assembly can then be dip coated again, such as to apply a thin coating of, for example, polyurethane, which will become the outer polymeric tubular member of the sheath. The sheath can then be removed from the mandrel.

Additionally, the intermediate tubular layer 28 can be, for example, braided or laser cut to form a pattern or structure, such that the intermediate tubular layer 28 is amenable to radial expansion. FIGS. 9-23 illustrate partial elevation views of various structures for the intermediate tubular layer. Some illustrated structures, such as those shown in FIGS. 11-14 and 23, include at least one discontinuity. For example, the struts 56, 58, 60, 62, 64 shown in FIGS. 11, 12, 13, 14, and 23, respectively, result in a discontinuous intermediate tubular layer 28 in that the struts 56, 58, 60, 62, 64 separate adjacent sections of the intermediate tubular layer 28 from each other, where the sections are spaced apart from each other along a longitudinal axis parallel to the lumen of the sheath. Thus, the structure of the intermediate tubular layer 28 can vary from section to section, changing along the length of the sheath.

The structures shown in FIGS. 9-23 are not necessarily drawn to scale. Components and elements of the structures can be used alone or in combination within a single intermediate tubular layer 28. The scope of the intermediate tubular layer 28 is not meant to be limited to these particular structures; they are merely exemplary embodiments.

Figure 24:
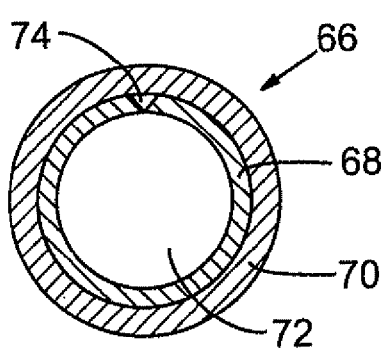
FIG. 24 illustrates a section view of one embodiment of a sheath having a longitudinal notch.
Figure 25:
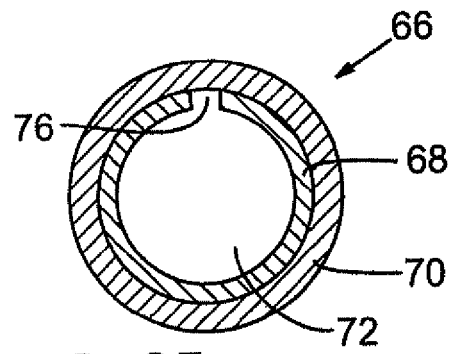
FIG. 25 shows a section view of one embodiment of a sheath having a longitudinal cut in the inner layer.
Figure 26:
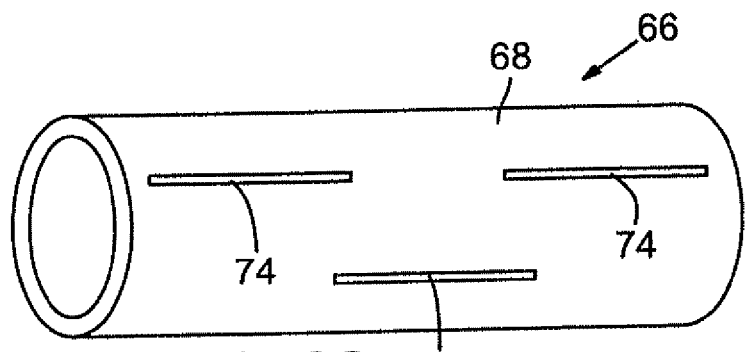
FIG. 26 shows a perspective view of one embodiment of a sheath having a plurality of notches or cuts in the outer tubular layer.

Alternative embodiments of a sheath for introducing a prosthetic device are also described. For example, FIGS. 24-26 illustrate a section view and a perspective view, respectively, of a sheath 66 for introducing a prosthetic device into a body. The sheath 66 comprises an inner layer, such as inner polymeric layer 68, an outer layer, such as polymeric tubular layer 70, and a hemostasis valve (not shown). The inner polymeric layer 68 and the outer polymeric tubular layer 70 at least partially enclose a lumen 72, through which a delivery apparatus and prosthetic device can pass from outside the patient's body into the patient's vessel. Either or both of the inner polymeric layer 68 and the outer polymeric layer 70 can be provided with at least one longitudinal notch and/or cut to facilitate radial expansion of the sheath.

For example, FIG. 24 illustrates a longitudinal notch 74 in the inner polymeric layer 68 that can facilitate radial expansion of the sheath 66. The longitudinal notch 74 can separate or split open completely upon application of a radial force due to insertion of a delivery apparatus or prosthetic device. Similarly, FIG. 25 illustrates a longitudinal cut 76 in the inner polymeric layer 68 that can also facilitate radial expansion of the sheath 66. The outer polymeric layer 70 can, additionally or alternatively, comprise one or more longitudinal cuts 76 or notches 74. Such cuts and/or notches, whether in the inner polymeric layer 68 or the outer polymeric layer 70, can extend substantially through the entire thickness of the layer, or can extend only partially through the thickness of the layer. The cuts and/or notches can be positioned at or near the inner or outer surface, or both surfaces, of the inner and/or outer polymeric layers 68, 70.

FIG. 26 illustrates a perspective view of one embodiment of an inner polymeric layer 68 with longitudinal notches 74 and a longitudinal cut 76. More or fewer notches 74 and/or cuts 76 can be provided. For clarity, the outer polymeric layer 70 is not shown in FIG. 26. As shown in FIG. 26, longitudinal notches 74 and/or cuts 76 can extend only along a portion of the length of sheath 66. In alternative embodiments, one or more notches 74 and/or cuts 76 can extend substantially along the entire length of the sheath 66. Additionally, notches 74 and/or cuts 76 can be positioned randomly or patterned.

One particular embodiment of a sheath 66 comprises a sheath having a notch or cut in the outer polymeric layer 70 or the inner polymeric layer 68 that extends longitudinally along approximately 75% of the length of the sheath 66. If such a notch or cut extends only partially through the associated layer, it can have a relatively low tear force, such as a tear force of about 0.5 lbs, so that the notch splits open relatively easily during use.

The inner polymeric layer 68 and the outer polymeric layer 70 can optionally be adhered together or otherwise physically associated with one another. The amount of adhesion between the inner polymeric layer 68 and the outer polymeric layer 70 can be variable over the surfaces of the layers. For example, little to no adhesion can be present at areas around or near any notches and/or cuts present in the layers, so as not to hinder radial expansion of the sheath 66. Adhesion between the layers can be created by, for example, thermal bonding and/or coatings. Embodiments of a sheath 66 can be formed from an extruded tube, which can serve as the inner polymeric layer 68. The inner polymeric layer 68 can be surface treated, such as by plasma etching, chemical etching or other suitable methods of surface treatment. By treating the surface of the inner polymeric layer 68, the outer surface of the inner polymeric layer 68 can have areas with altered surface angles that can provide better adhesion between the inner polymeric layer 68 and the outer polymeric layer 70. The treated inner polymeric layer can be dip coated in, for example, a polyurethane solution to form the outer polymeric layer 70. In some configurations, the polyurethane may not adhere well to untreated surface areas of the inner polymeric layer 68. Thus, by surface treating only surface areas of the inner polymeric layer 68 that are spaced away from the areas of expansion (e.g. the portion of the inner polymeric layer 68 near notches 74 and/or cuts 76), the outer polymeric layer 70 can be adhered to some areas of the inner polymeric layer 68, while other areas of the inner polymeric layer 68 remain free to slide relative to the outer polymeric layer 70, thus allowing for expansion of the diameter of the sheath 66. Thus, areas around or near any notches 74 and/or cuts 76 can experience little to no adhesion between the layers, while other areas of the inner and outer polymeric layers 68, 70 can be adhesively secured or otherwise physically associated with each other.

As with previously disclosed embodiments, the embodiments illustrated in FIGS. 24-26 can be applied to sheaths having a wide variety of inner and outer diameters. Applications can utilize a sheath of the present disclosure with an inner diameter of the inner polymeric layer 68 that is expandable to an expanded diameter of from about 3 Fr to about 26 Fr. The expanded diameter can vary slightly along the length of the sheath 66. For example, the expanded outer diameter at the proximal end of the sheath 66 can range from about 3 Fr to about 28 Fr, while the expanded outer diameter at the distal end of the sheath 66 can range from about 3 Fr to about 25 Fr. Embodiments of a sheath 66 can expand to an expanded outer diameter that is from about 10% greater than the original unexpanded outer diameter to about 100% greater than the original unexpanded outer diameter.

In some embodiments, the outer diameter of the sheath 66 gradually decreases from the proximal end of the sheath 66 to the distal end of the sheath 66. For example, in one embodiment, the outer diameter can gradually decrease from about 26 Fr at the proximal end to about 18 Fr at the distal end. The diameter of the sheath 66 can transition gradually across substantially the entire length of the sheath 66. In other embodiments, the transition or reduction of the diameter of the sheath 66 can occur only along a portion of the length of the sheath 66. For example, the transition can occur along a length from the proximal end to the distal end, where the length can range from about 0.5 inches to about the entire length of sheath 66.

Suitable materials for the inner polymeric layer 68 can have a high elastic strength and include materials discussed in connection with other embodiments, especially Teflon (PTFE), polyethylene (e.g. high density polyethylene), fluoropolymers, or combinations thereof. In some embodiments, the inner polymeric layer 68 preferably has a low coefficient of friction, such as a coefficient of friction of from about 0.01 to about 0.5. Some preferred embodiments of a sheath 66 comprise an inner polymeric layer 68 having a coefficient of friction of about 0.1 or less.

Likewise, suitable materials for the outer polymeric layer 70 include materials discussed in connection with other embodiments, and other thermoplastic elastomers and/or highly elastic materials.

The Shore hardness of the outer polymeric layer 70 can be varied for different applications and embodiments. Some embodiments include an outer polymeric layer with a Shore hardness of from about 25 A to about 80 A, or from about 20 D to about 40 D. One particular embodiment comprises a readily available polyurethane with a Shore hardness of 72 A. Another particular embodiment comprises a polyethylene inner polymeric layer dipped in polyurethane or silicone to create the outer polymeric layer.

The sheath 66 can also include a radiopaque filler or marker as described above. In some embodiments, a distinct radiopaque marker or band can be applied to some portion of the sheath 66. For example, a radiopaque marker can be coupled to the inner polymeric layer 68, the outer polymeric layer 70, and/or can be positioned in between the inner and outer polymeric layers 68, 70.

Figure 27A:
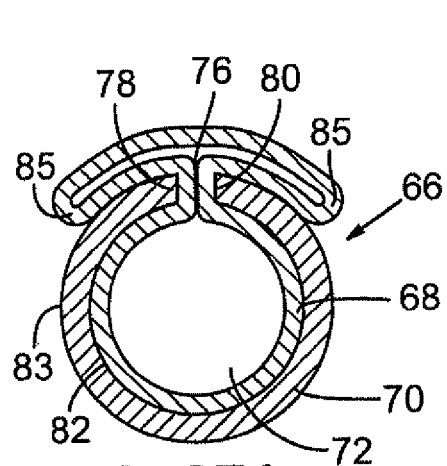
FIG. 27 illustrates a section view of one embodiment of a sheath, wherein the outer tubular layer contains a longitudinal cut, and the inner layer extends into the gap created by the cut in the outer tubular layer, in an unexpanded configuration.
Figure 28:
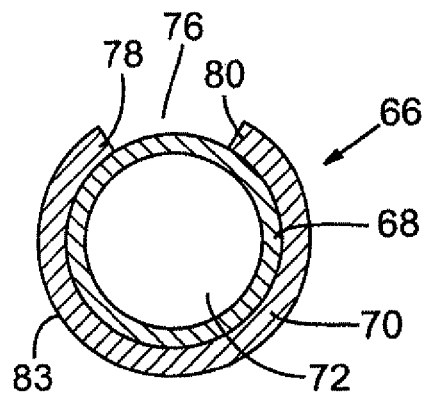
FIG. 28 shows a section view of the sheath of FIG. 27 in an expanded configuration.

FIGS. 27A-27E and 28 illustrate section views of various embodiments of unexpanded (FIGS. 27A-27E) and expanded (FIG. 28) sheaths 66 according to the present disclosure. The sheath 66 includes a split outer polymeric tubular layer 70 having a longitudinal cut 76 through the thickness of the outer polymeric tubular layer 70 such that the outer polymeric tubular layer 70 comprises a first portion 78 and a second portion 80 separable from one another along the cut 76. An expandable inner polymeric layer 68 is associated with an inner surface 82 of the outer polymeric tubular layer 70, and, in the unexpanded configuration shown in FIG. 27, a portion of the inner polymeric layer 68 extends through a gap created by the cut 76 and can be compressed between the first and second portions 78, 80 of the outer polymeric tubular layer 70. Upon expansion of the sheath 66, as shown in FIG. 28, first and second portions 78, 80 of the outer polymeric tubular layer 70 have separated from one another, and the inner polymeric layer 68 is expanded to a substantially cylindrical tube. In some embodiments, two or more longitudinal cuts 76 may be provided through the thickness of the outer polymeric tubular layer 70. In such embodiments, a portion of the inner polymeric layer 68 may extend through each of the longitudinal cuts 76 provided in the outer polymeric tubular layer 70.

Figure 27B:
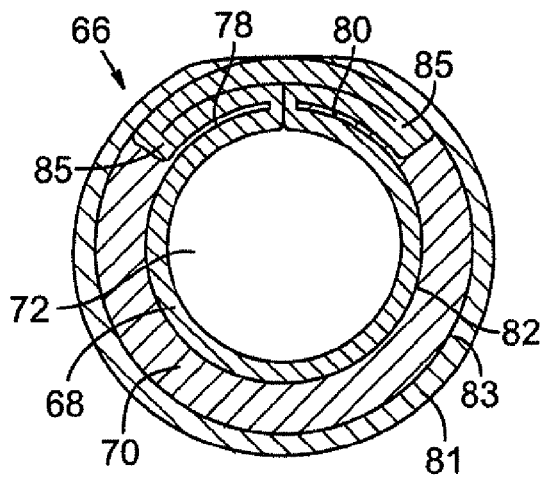
Figure 27C:
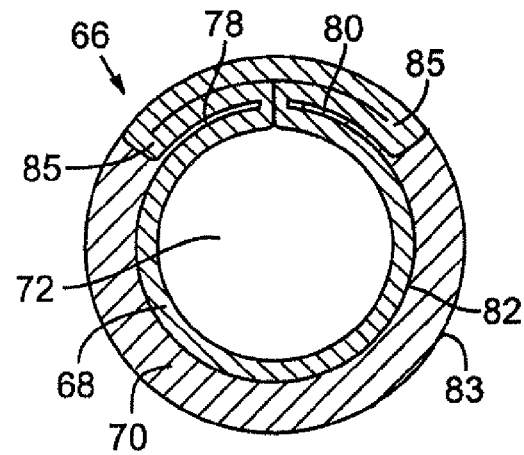
Figure 27D:
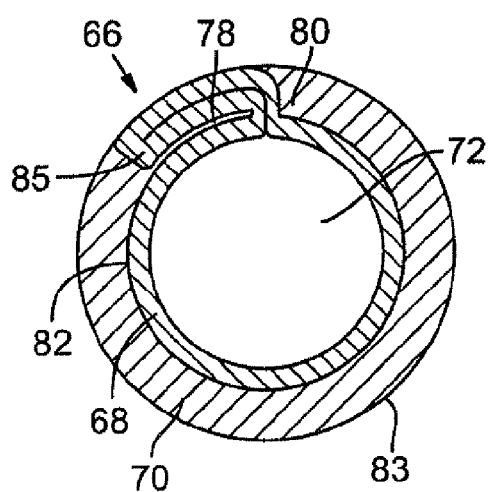
Figure 27E:
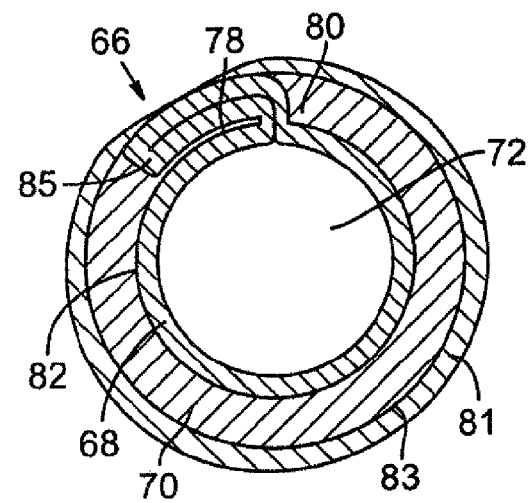

Preferably, the inner polymeric layer 68 comprises one or more materials that are elastic and amenable to folding and/or pleating. For example, FIG. 27A illustrates an inner polymeric layer 68 with folded regions 85. As seen in FIGS. 27A-27E, the sheath 66 can be provided with one or more folded regions 85. Such folded regions 85 can be provided along a radial direction and substantially conform to the circumference of the outer polymeric tubular layer 70. At least a portion of the folded regions 85 can be positioned adjacent the outer surface 83 of the outer polymeric tubular layer 70. Additionally, as shown in FIGS. 27B and 27E, at least a portion of the folded region or regions 85 can be overlapped by an outer covering, such as outer polymeric covering 81. The outer polymeric covering 81 can be adjacent at least a portion of the outer surface 83 of the outer polymeric tubular layer 70. The outer polymeric covering 81 serves to at least partially contain the folded regions 85 of the inner polymeric layer 68, and can also prevent the folded regions 85 from separating from the outer polymeric tubular layer 70 when, for example, the sheath 66 undergoes bending. In some embodiments, the outer polymeric covering 81 can be at least partially adhered to the outer surface 83 of the outer polymeric tubular layer 70. The outer polymeric covering 81 can also increase the stiffness and/or durability of the sheath 66. Additionally, as shown in FIGS. 27B and 27E, the outer polymeric covering 81 may not entirely overlap the circumference of the sheath 66. For example, the outer polymeric covering 81 may be provided with first and second ends, where the ends do not contact one another. In these embodiments, only a portion of the folded region 85 of the inner polymeric layer 68 is overlapped by the outer polymeric covering 81.

In embodiments having a plurality of folded regions 85, the regions can be equally displaced from each other around the circumference of the outer polymeric tubular layer 70. Alternatively, the folded regions can be off-center, different sizes, and/or randomly spaced apart from each other. While portions of the inner polymeric layer 68 and the outer tubular layer 70 can be adhered or otherwise coupled to one another, the folded regions 85 preferably are not adhered or coupled to the outer tubular layer 70. For example, adhesion between the inner polymeric layer 68 and the outer tubular layer 70 can be highest in areas of minimal expansion.

One particular embodiment of the sheath illustrated in FIGS. 27-28 comprises a polyethylene (e.g. high density polyethylene) outer polymeric tubular layer 70 and a PTFE inner polymeric layer 68. However, other materials are suitable for each layer, as described above. Generally, suitable materials for use with the outer polymeric tubular layer 70 include materials having a high stiffness or modulus of strength that can support expansion and contraction of the inner polymeric layer 68.

In some embodiments, the outer polymeric tubular layer 70 comprises the same material or combination of materials along the entire length of the outer polymeric tubular layer 70. In alternative embodiments, the material composition can change along the length of the outer polymeric tubular layer 70. For example, the outer polymeric tubular layer can be provided with one or more segments, where the composition changes from segment to segment. In one particular embodiment, the Durometer rating of the composition changes along the length of the outer polymeric tubular layer 70 such that segments near the proximal end comprise a stiffer material or combination of materials, while segments near the distal end comprise a softer material or combination of materials. This can allow for a sheath 66 having a relatively stiff proximal end at the point of introducing a delivery apparatus, while still having a relatively soft distal tip at the point of entry into the patient's vessel.

As with other disclosed embodiments, the embodiments of sheath 66 shown in FIGS. 27-28 can be provided in a wide range of sizes and dimensions. For example, the sheath 66 can be provided with an unexpanded inner diameter of from about 3 Fr to about 26 Fr. In some embodiments, the sheath 66 has an unexpanded inner diameter of from about 15 Fr to about 16 Fr. In some embodiments, the unexpanded inner diameter of the sheath 66 can range from about 3 Fr to about 26 Fr at or near the distal end of sheath 66, while the unexpanded inner diameter of the sheath 66 can range from about 3 Fr to about 28 Fr at or near the proximal end of sheath 66. For example, in one unexpanded embodiment, the sheath 66 can transition from an unexpanded inner diameter of about 16 Fr at or near the distal end of the sheath 66 to an unexpanded inner diameter of about 26 Fr at or near the proximal end of the sheath 66.

The sheath 66 can be provided with an unexpanded outer diameter of from about 3 Fr to about 30 Fr, and, in some embodiments has an unexpanded outer diameter of from about 18 Fr to about 19 Fr. In some embodiments, the unexpanded outer diameter of the sheath 66 can range from about 3 Fr to about 28 Fr at or near the distal end of sheath 66, while the unexpanded outer diameter of the sheath 66 can range from about 3 Fr to about 30 Fr at or near the proximal end of sheath 66. For example, in one unexpanded embodiment, the sheath 66 can transition from an unexpanded outer diameter of about 18 Fr at or near the distal end of the sheath 66 to an unexpanded outer diameter of about 28 Fr at or near the proximal end of the sheath 66.

The thickness of the inner polymeric layer 68 can vary, but in some preferred embodiments is from about 0.002 inches to about 0.015 inches. In some embodiments, expansion of the sheath 66 can result in expansion of the unexpanded outer diameter of from about 10% or less to about 430% or more.

As with other illustrated and described embodiments, the embodiments shown in FIGS. 27-28 can be provided with a radiopaque filler and/or a radiopaque tip marker as described above. The sheath 66 can be provided with a radiopaque tip marker provided at or near the distal tip of the sheath 66. Such a radiopaque tip marker can comprise materials such as those suitable for the radiopaque filler, platinum, iridium, platinum/iridium alloys, stainless steel, other biocompatible metals, or combinations thereof.

Figure 29A:
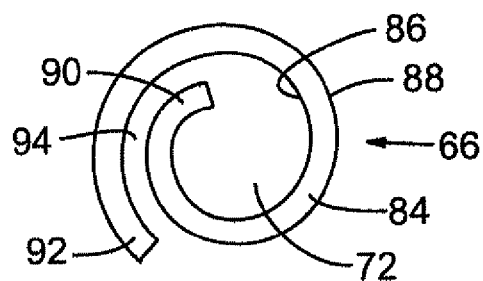
FIGS. 29A-29D show section views of various embodiments of a sheath having overlapping sections.
Figure 29B:
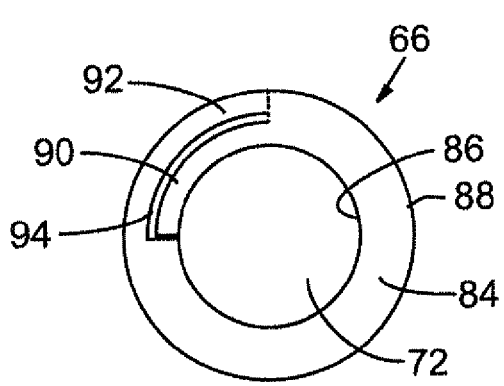
Figure 29C:
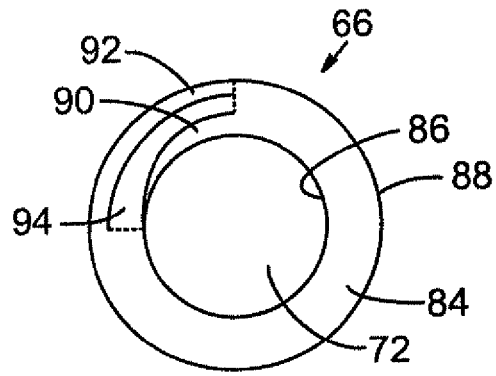
Figure 29D:
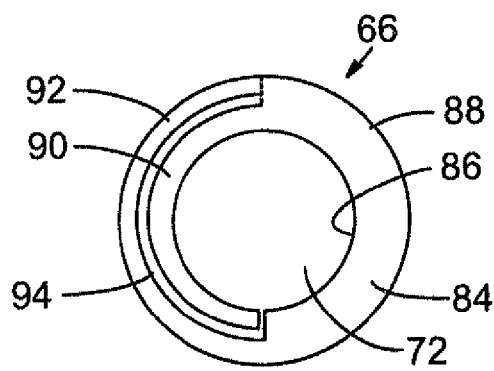

FIGS. 29A-29D show section views of other possible configurations of a sheath 66 for introducing a prosthetic device into a patient's vasculature. The sheath 66 comprises a polymeric tubular layer 84 having an inner surface 86 and an outer surface 88. The thickness of the polymeric tubular layer 84 extends from the inner surface 86 to the outer surface 88. As shown in FIGS. 29B-29D, the polymeric tubular layer 84 can be formed with at least a first angular portion 90 of reduced thickness adjacent the inner surface 86 and a second angular portion 92 of reduced thickness adjacent the outer surface 88, with the second portion 92 at least partially overlapping the first portion 90. FIG. 29A illustrates a similar configuration, where a second portion 92 at least partially overlaps a first portion 90 in a partial coil configuration. In the embodiment of FIG. 29A, the second portion 92 and the first portion 90 can have the same thickness.

In preferred embodiments, the first and second portions 90, 92 are not adhered to one another. In some embodiments, and best seen in FIG. 29A, there can be a small gap 94 between the first and second portions 90, 92 that can give the sheath 66 the appearance of having two interior lumens 72, 94. FIGS. 29A-29D illustrate the sheath 66 in unexpanded configurations. Preferably, upon expansion of the sheath 66, the ends of the first and second portions 90, 92 abut or are in close proximity to each other to reduce or eliminate any gap between them.

In some embodiments, a sheath 66 can comprise a partial slit or score line along at least a portion of its length. For example, as shown in FIG. 33, a sheath 66 can comprise an outer polymeric tubular layer 70 over an inner polymeric layer 68. The inner polymeric layer can extend through a cut in the outer polymeric tubular layer 70, to form a folded region 85 on the outer surface of the outer polymeric tubular layer 70, such as also shown in FIG. 27C. The folded region 85 of the inner layer, in some embodiments, terminates before the outer polymeric tubular layer 70 (i.e. the outer polymeric tubular layer 70 is longer than the inner layer). As shown in FIG. 33, in these embodiments, the sheath 66 can comprise a partial slit or score line 77 that can extend from the termination (distal end) 75 of the folded region 85 to the distal end 40 of the sheath 66. In some embodiments, score line 77 can facilitate expansion of the sheath 66.

Score line 77 can be substantially centrally located with respect to the folded region 85. In alternative embodiments, score line 77 can be positioned in other locations relative to the folded region 85. Also, sheath 66 can comprise one or more score lines 77. For example, as shown in FIG. 34, one or more score lines 77 can be peripherally located with respect to the folded region 85. The one or more score lines 77 can be positioned anywhere around the circumference of the outer polymeric tubular layer 70. In embodiments comprising a radiopaque marker 69 as seen in FIG. 33, a score line 77 can extend from, for example, the distal end of the radiopaque marker 69 substantially to the distal end 40 of the sheath 66.

Various methods can be used to produce the sheaths discussed above and below, throughout the present disclosure. For example, a method of making the sheath shown in FIGS. 2A-2D can comprise providing a mandrel and applying an inner layer on the mandrel, such as by spray coating or dip coating the mandrel. An intermediate layer, such as a mesh structure, can then be mounted on the inner layer. An outer layer can be applied over the intermediate layer, such as by a second spray coating or dip coating step. Methods can comprise etching or surface treating at least a portion of the inner layer. Also, methods can comprise providing one or more notches and/or cuts in the inner layer and/or the outer layer. Cuts and/or notches can be provided by, for example, laser cutting or etching one or more layers.

In some embodiments of methods of making a sheath such as the sheaths illustrated in FIGS. 2A-2D, layers can be preformed and mounted on a mandrel, and then fused or thermally bonded together. For examples in one method, an inner layer is applied to a mandrel. An intermediate layer can be applied to the outer surface of the inner layer. An outer layer can be applied to the outer surface of the intermediate layer. Heat shrink tubing can be applied, and the assembly heated, such that the inner layer, the intermediate layer, and/or the outer layer are thermally bonded and compressed together under the heat shrink tubing.

Figure 30:
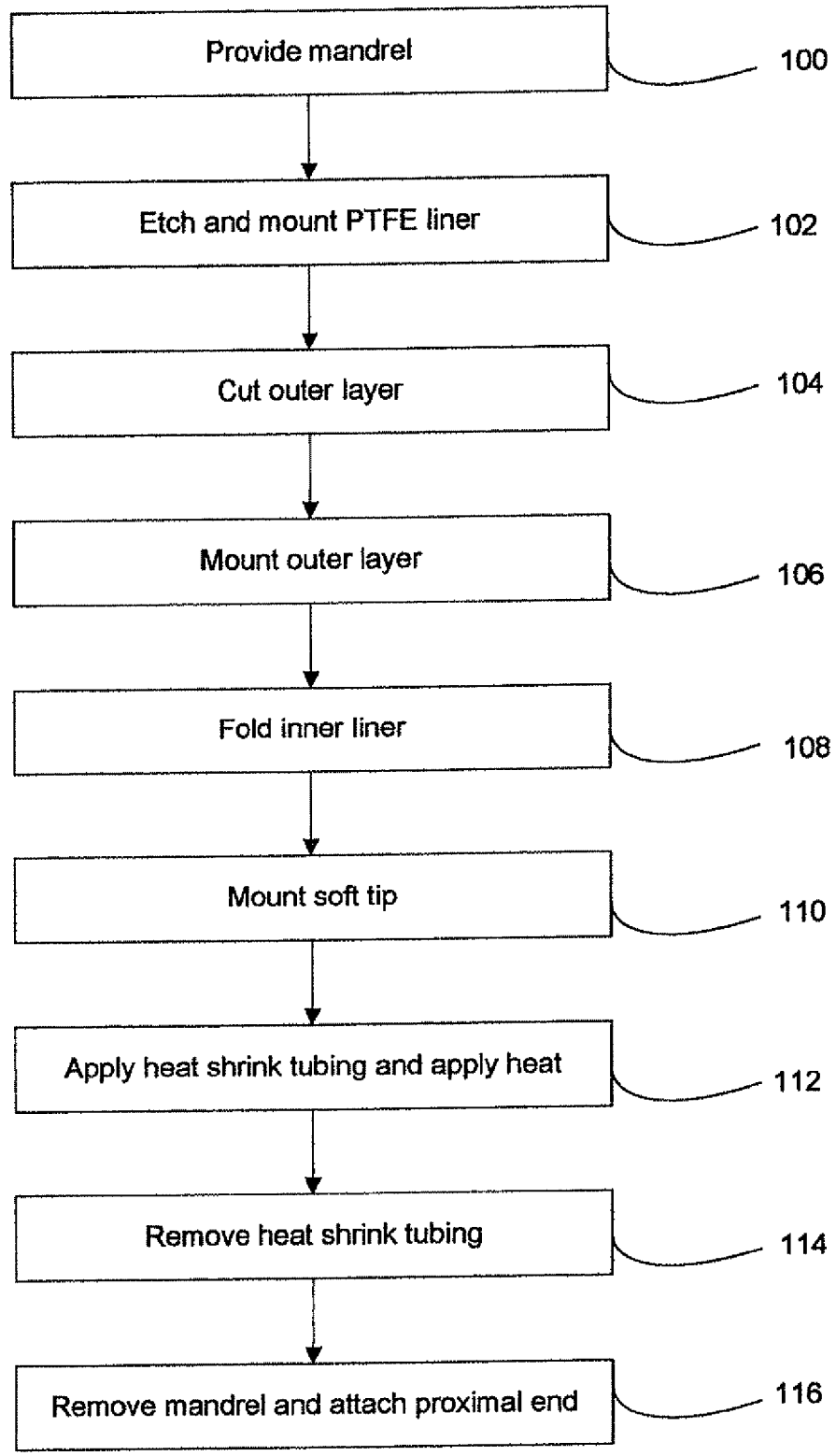
FIG. 30 illustrates a block diagram of one embodiment of a method of making a sheath according to the present disclosure.
Figure 32A:
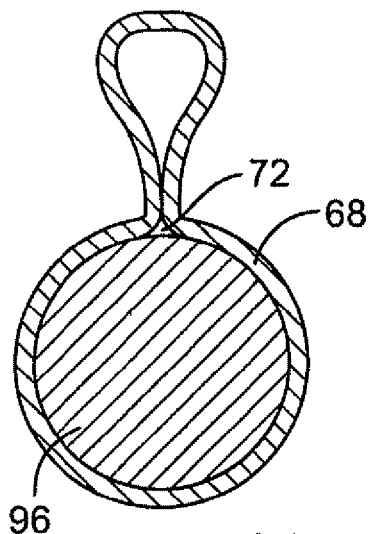
FIGS. 32A-32H illustrate section or elevation views of various method steps of the methods shown in FIGS. 30-31.

FIG. 30 illustrates a block diagram of one method of producing a sheath for use with a delivery apparatus in minimally invasive surgery. One or more mandrels can be provided (step 100). The mandrel can be provided with an exterior coating, such as a Teflon® coating, and the mandrel's diameter can be predetermined, based on the desired size of the resulting sheath. A liner that will become the inner polymeric layer of the sheath, such as a PTFE or high density polyethylene liner, can be mounted on the mandrel (step 102). The liner can be etched and/or surface treated prior to being mounted on the mandrel, according to conventional etching and surface treatment methods. FIG. 32A illustrates a section view of a sheath at steps 100 and 102 of FIG. 30. A coated mandrel 96 is inserted within the lumen 72 of the inner polymeric layer 68. The circumference of the inner polymeric layer 68 is larger than the circumference of the mandrel 96, such that an excess portion of the inner polymeric layer 68 can be gathered above the mandrel 96.

A layer of material that will become the outer polymeric tubular layer, such as a layer comprising polyurethane or polyolefin, can be cut or notched through all, substantially all, or a part of the thickness of the layer (step 104). Such a cut or notch can extend longitudinally along the length of the layer and can extend along substantially the entire length of the outer polymeric tubular layer. In alternative embodiments, the cut or notch can be provided along only a portion of the outer polymeric tubular layer. For example, the outer polymeric tubular layer can be cut starting at the distal end of the outer polymeric tubular layer, with the cut ending before the proximal end of the outer polymeric tubular layer. In one embodiment, the cut can end at a transition, where the outer diameter of the outer polymeric tubular layer increases or decreases. In one specific embodiment, the cut or notch can extend longitudinally along about 75% of the length of the sheath.

Figure 32B:
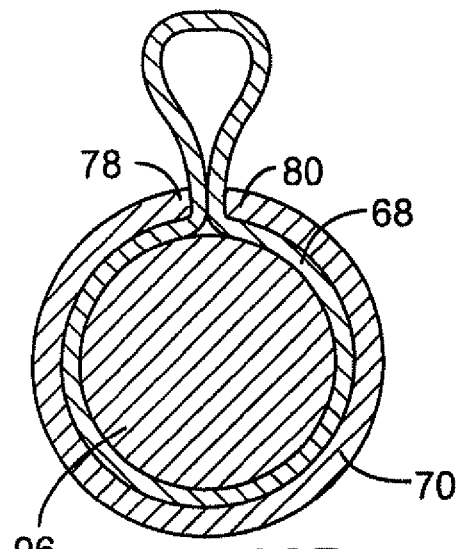

The cut or notched outer polymeric tubular layer can be applied, positioned, adhered, mounted, thermally fused or bonded, dip coated, and/or otherwise coupled to the etched inner liner (step 106). FIG. 32B shows a section view of the sheath at step 106 of FIG. 30, with outer polymeric tubular layer 70 applied to the inner polymeric layer 68 such that a portion of the inner polymeric layer 68 extends between the cut formed between first and second portions 78, 80 of the outer polymeric tubular layer 70.

Figure 32C:
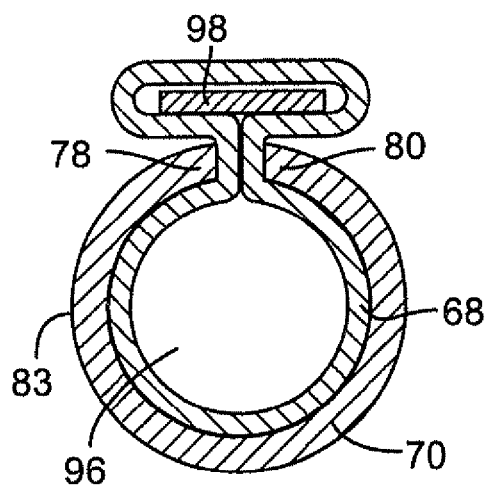
Figure 32D:
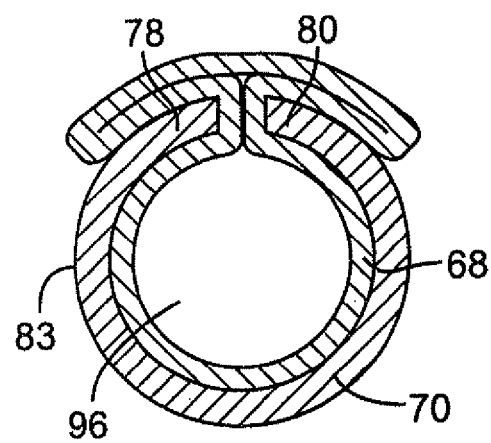
Figure 32E:
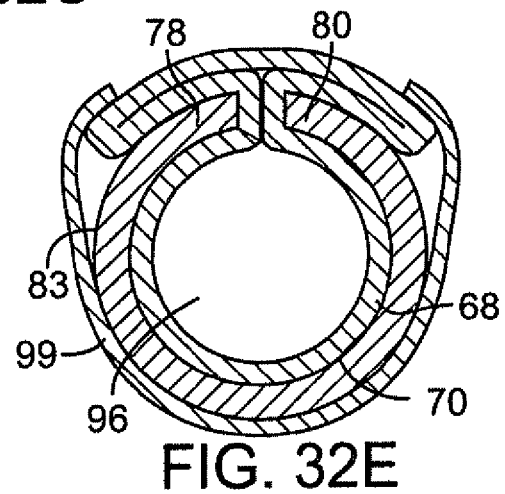

In alternative embodiments, the outer polymeric tubular layer can be notched or cut after being mounted on the inner liner/mandrel assembly. The outer polymeric tubular layer can optionally be provided with a hydrophilic coating and/or provided with additional layers, such as being dip coated with polyurethane. Some portion of the inner liner can protrude through the cut in the outer polymeric tubular layer after such outer polymeric tubular layer is mounted onto the inner liner/mandrel arrangement. Using, for example, a split tool, the protruding portion of the inner liner can be folded down onto the outer surface of the outer polymeric tubular layer (step 108). In some embodiments, the protruding portion of the inner liner is folded down along the entire length of the resulting sheath, while in other embodiments, the protruding portion of the inner liner is only present along a portion of the length of the sheath, or is only folded down along a portion of the length of the resulting sheath. FIG. 32C shows a section view of the sheath at step 108 of FIG. 30. A split tool 98 is used to fold the excess portion of inner polymeric layer 68 over a portion of the outer surface 83 of the outer polymeric tubular layer 70. FIG. 32D shows a section view of the sheath after completion of step 108 of FIG. 30. Split tool 98 has been removed, and folding of the excess portion of the inner polymeric layer 68 has been completed. FIG. 32E shows a section view of an outer covering, such as outer polymeric covering 99, that can be applied such that it overlaps a portion of the folded portion of inner polymeric layer 68. The outer polymeric covering 99 contacts at least a portion of the outer surface 83 of the outer polymeric tubular layer 70.

A soft, atraumatic tip can be provided at the distal end of the resulting sheath (step 110). Additional outer layers can also be applied, if desired. Then, a layer of heat shrink tubing, such as fluorinated ethylene propylene (FEP) heat shrink tubing, can be positioned over the entire assembly (step 112). An appropriate amount of heat is applied, thus shrinking the heat shrink tubing and compressing the layers of the sheath together, such that components of the sheath can be thermally bonded or fused together where desired. Once the components of the sheath have been bonded together, the heat shrink tubing can be removed (step 114). Finally, the proximal end of the sheath can be adhered or otherwise attached to a housing of a catheter assembly, and the sheath can be removed from the mandrel (step 116).

Figure 31:
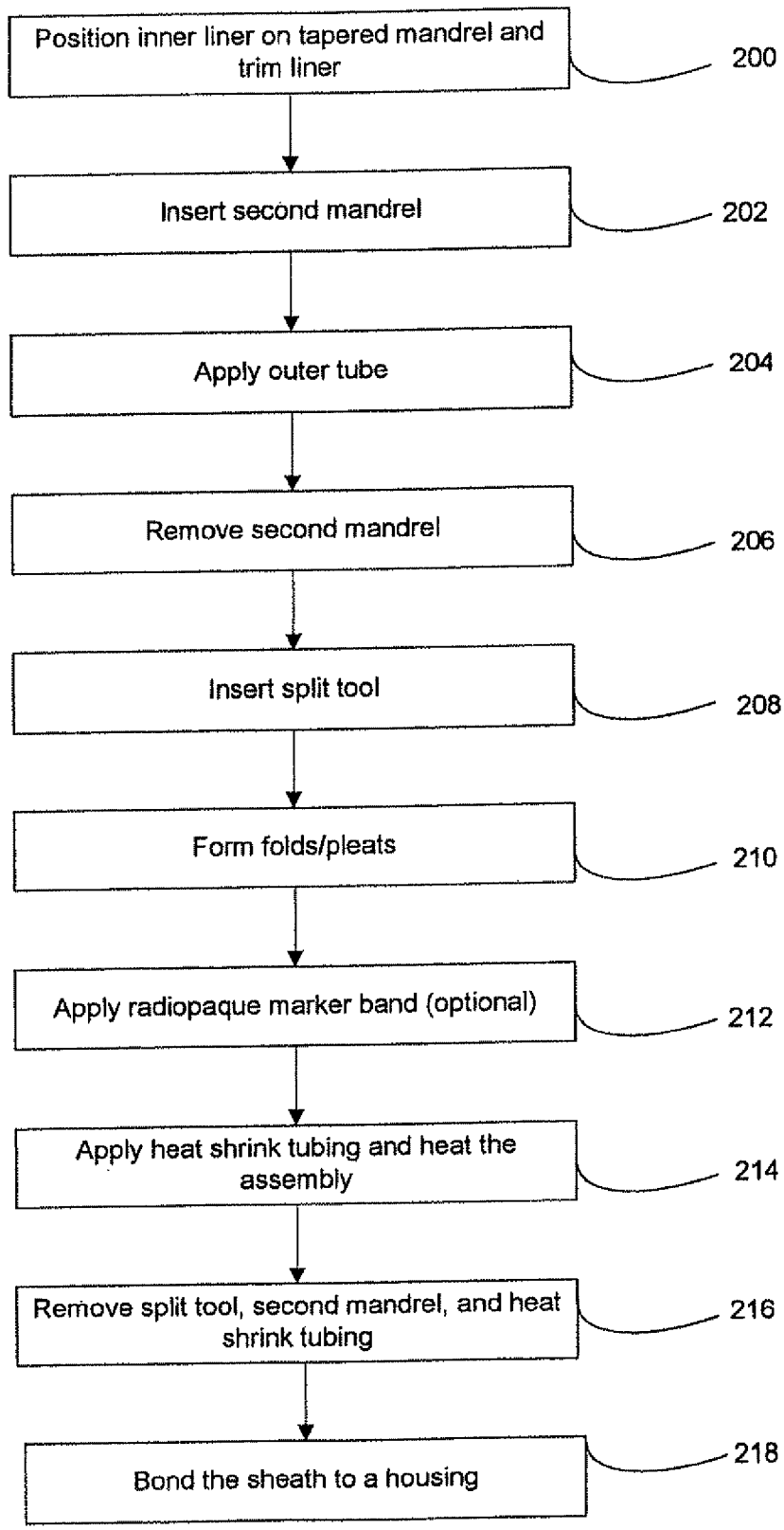
FIG. 31 illustrates a block diagram of another embodiment of a method of making a sheath according to the present disclosure.
Figure 32F:
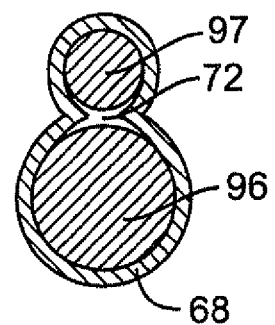

FIG. 31 illustrates a block diagram of an alternative embodiment of a method of making a sheath. An inner liner, such as an etched PTFE tubing can be applied to a tapered mandrel, such as a 16 Fr tapered mandrel, and trimmed to an appropriate length (step 200). A second mandrel, such as a 0.070 inches diameter mandrel, can be inserted in the lumen of the inner liner such that the mandrels are arranged side by side in the inner liner (step 202). FIG. 32F shows a section view of a sheath at steps 200 and 202 of FIG. 31. An inner liner or inner polymeric layer 68 is applied on a first, tapered, mandrel 96. A second mandrel 97 is inserted into the lumen 72 of the inner polymeric layer 68 created by the excess portion of the inner polymeric layer 68, as described.

Figure 32G:
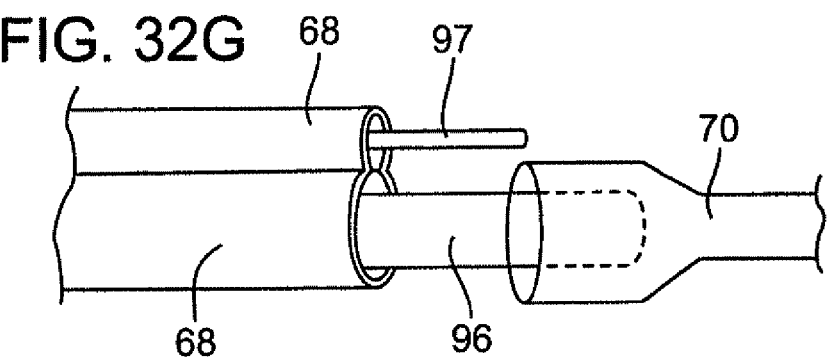

A notched or cut outer polymeric tubular layer, such as high density polyethylene tubing that has been notched or cut longitudinally, can be slid onto the tapered mandrel and a portion of the inner liner, starting at the distal end of the tapered mandrel (step 204). The second mandrel can then be removed (step 206). FIG. 32G illustrates a perspective view of the sheath at steps 204 and 206 of FIG. 31. A polymeric outer tubular layer 70 having a longitudinal cut is applied over the tapered mandrel 96 and inner polymeric layer 68. The outer tubular layer conforms to the portion of the inner polymeric layer around the tapered mandrel 96, and the portion of the inner polymeric layer 68 around the second mandrel 97 extends through the longitudinal cut in the outer polymeric tubular layer 70.

A split tool can be inserted into the portion of the lumen of the inner liner that was previously occupied by the second mandrel (step 208). The split tool can then be used to form folds and/or pleats in the excess portion of the inner liner which now extends through the longitudinal cut in the outer polymeric tubular layer (step 210). A radiopaque marker band can optionally be applied at the distal end of the sheath (step 212). Heat shrink tubing, such as FEP heat shrink tubing, can be applied over the entire sheath, and heat can be applied to compress the components of the sheath and bond or fuse them together (step 214). The split tool, heat shrink tubing, and second mandrel can then be removed (step 216). The sheath can then be utilized with a delivery apparatus, such as by bonding the proximal end of the sheath to a polycarbonate housing of a delivery apparatus or catheter assembly (step 218).

Figure 32H:
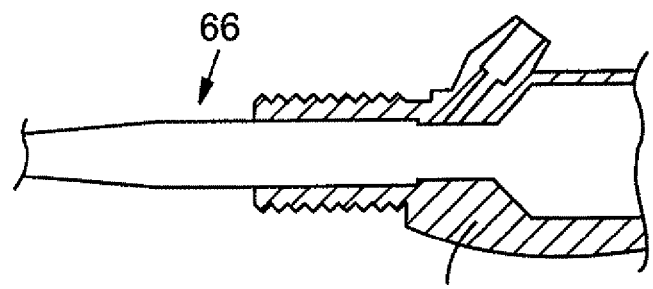

FIG. 32H illustrates an elevation view of the sheath at step 218 of FIG. 31. The sheath 66, made according to described methods and processes, can be attached or bonded to a housing 101, such as by bonding the proximal end of the sheath 66 to the polycarbonate housing 101.

Sheaths of the present disclosure can be used with various methods of introducing a prosthetic device into a patient's vasculature. One such method comprises positioning an expandable introducer sheath in a patient's vessel, passing a device through the introducer sheath, which causes a portion of the introducer sheath surrounding the device to expand and accommodate the profile of the device, and automatically retracting the expanded portion of the introducer sheath to its original size after the device has passed through the expanded portion.

Some specific methods comprise delivering a tissue heart valve to a patient. Such methods can additionally comprise placing the tissue heart valve in a crimped state on the distal end portion of an elongated delivery apparatus, and inserting the elongated delivery device with the crimped valve into the introducer sheath. Next, the delivery apparatus can be advanced through the patient's vasculature to the treatment site, where the valve can be implanted.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A sheath for introducing a prosthetic device into a body, comprising:
    a substantially circumferentially continuous inner tubular layer comprising at least one longitudinal pleat;
    an outer tubular layer; and
    a lumen enclosed by the inner tubular layer and the outer tubular layer,
    wherein the outer tubular layer contains a longitudinal cut through it such that the outer tubular layer comprises a first longitudinal edge, a second longitudinal edge, and a gap there between, the longitudinal cut facilitating radial expansion of the sheath,
    wherein a portion of the at least one longitudinal pleat extends into the gap, wherein the portion of the at least one longitudinal pleat extending into the gap extends through the gap to an outer surface of the outer tubular layer in a non-expanded configuration,
    wherein a portion of the sheath enclosed by both the inner tubular layer and the outer tubular layer, and surrounding a prosthetic device passing through the lumen expands to accommodate a profile of the prosthetic device, and
    wherein the expanded portion of the sheath automatically contracts after the prosthetic device passes therethrough.

2. The sheath of claim 1, further comprising an outer covering over at least a portion of the outer surface of the outer tubular layer, wherein the outer covering overlaps at least a portion of the at least one longitudinal pleat of the inner tubular layer.

3. The sheath of claim 1, wherein at least a portion of an outer surface of the inner tubular layer is surface treated or etched, and wherein the inner tubular layer and the outer tubular layer are adhesively secured to each other substantially only at the portion that is surface treated or etched so as to substantially avoid interference with radial expansion of the sheath.

4. The sheath of claim 1, wherein the inner tubular layer comprises PTFE.

5. The sheath of claim 1, wherein the outer tubular layer comprises high density polyethylene.

6. The sheath of claim 1, further comprising at least one radiopaque marker or filler.

7. The sheath of claim 1, further comprising a lubricating liner on at least a portion of an inner surface of the inner tubular layer.

8. The sheath of claim 1, further comprising a hydrophilic coating on at least a portion of the outer surface of the outer tubular layer.

9. A method of introducing a prosthetic device into a patient's vasculature, the method comprising:
    positioning at least part of the expandable sheath of claim 1 in a patient's vessel;
    introducing the device into the lumen of the expandable sheath;
    expanding a portion of the sheath via radial force applied by the device at the location of the expanded portion;
    moving the device through the expanded portion; and
    at least partially collapsing the expanded portion of the sheath after the device has passed through the expanded portion.

10. The sheath of claim 1, wherein the outer tubular layer comprises polyurethane.

11. The sheath of claim 10, wherein the outer tubular layer further comprises high density polyethylene.

12. The sheath of claim 1, wherein an unexpanded inner diameter of the sheath is from about 3 Fr to about 26 Fr.

13. The sheath of claim 12, wherein the unexpanded inner diameter of the sheath is from about 15 Fr to about 16 Fr.

14. The sheath of claim 1, wherein the first longitudinal edge of the outer tubular layer at least partially overlaps the second longitudinal edge of the outer tubular layer.

15. The sheath of claim 1, wherein at least a portion of the first longitudinal edge of the outer tubular layer is thinner relative to a non-longitudinal-edge portion of the outer tubular layer.

16. The sheath of claim 15, wherein at least a portion of the second longitudinal edge of the outer tubular layer is thinner relative to the non-longitudinal-edge portion of the outer tubular layer.

17. The sheath of claim 1, wherein the inner tubular layer is expandable into a substantially cylindrical tube in an expanded configuration.

18. A sheath for introducing a prosthetic device into a body, comprising:
- a substantially circumferentially continuous PTFE inner tubular layer comprising at least one longitudinal pleat;
- an outer tubular layer comprising high density polyethylene and polyurethane; and
- a lumen enclosed by the inner tubular layer and the outer tubular layer,
wherein
- the outer tubular layer contains a longitudinal cut through it such that the outer tubular layer comprises a first longitudinal edge, a second longitudinal edge, and a gap therebetween, the first longitudinal edge at least partially overlapping the second longitudinal edge, the longitudinal cut facilitating radial expansion of the outer tubular layer,
- a portion of the at least one longitudinal pleat extends into the gap, wherein the portion of the at least one longitudinal pleat extending into the gap extends through the gap to an outer surface of the outer tubular layer in a non-expanded configuration,
- a portion of the sheath enclosed by both the inner tubular layer and the outer tubular layer, and surrounding a prosthetic device passing through the lumen expands to accommodate a profile of the prosthetic device, and
- the expanded portion of the sheath automatically contracts after the prosthetic device passes therethrough.

* * * * *